(12) United States Patent
Herron et al.

(10) Patent No.: US 6,242,267 B1
(45) Date of Patent: *Jun. 5, 2001

(54) OSCILLATION APPARATUS AND METHODS FOR MULTI-ANALYTE HOMOGENEOUS FLUORO-IMMUNOASSAYS

(75) Inventors: James N. Herron; Douglas A. Christensen, both of Salt Lake City; Scott D. Miles, Sandy, all of UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/142,946
(22) PCT Filed: Mar. 19, 1997
(86) PCT No.: PCT/US97/04378
  § 371 Date: Sep. 18, 1998
  § 102(e) Date: Sep. 18, 1998
(87) PCT Pub. No.: WO97/35203
  PCT Pub. Date: Sep. 25, 1997

Related U.S. Application Data
(60) Provisional application No. 60/014,713, filed on Mar. 19, 1996.

(51) Int. Cl.⁷ .......................... G01N 33/552; G01N 33/53
(52) U.S. Cl. .............. 436/527; 422/55; 422/56; 422/57; 422/58; 422/102; 435/5; 435/7.1; 435/7.2; 435/7.5; 435/287.1; 435/808; 435/287.2; 435/288.5; 435/288.7; 436/164; 436/172; 436/265; 436/518; 436/524; 436/527; 436/528; 436/531; 436/807; 356/426; 356/427
(58) Field of Search ..................... 422/55, 56, 57, 422/58, 102; 435/5, 7.1, 7.2, 7.5, 287.1, 287.2, 808, 288.5, 288.7; 436/164, 165, 172, 518, 527, 528, 524, 531, 807; 356/427, 426

(56) References Cited

U.S. PATENT DOCUMENTS

| | | | |
|---|---|---|---|
| 4,880,752 | * 11/1989 | Keck et al. | 435/7 |
| 5,081,012 | * 1/1992 | Flanagan et al. | 435/7.9 |
| 5,156,976 | * 10/1992 | Slovacek et al. | 436/164 |
| 5,344,784 | * 9/1994 | Attridge | 436/518 |
| 5,637,469 | * 6/1997 | Wilding et al. | 435/7.21 |
| 5,639,428 | * 6/1997 | Cottingham et al. | 422/112 |
| 5,731,212 | * 3/1998 | Gavin et al. | 436/526 |
| 5,919,712 | * 6/1999 | Herron et al. | 436/518 |

* cited by examiner

Primary Examiner—Long V. Le
Assistant Examiner—Jennifer Russert
(74) Attorney, Agent, or Firm—Trask Britt

(57) ABSTRACT

An apparatus and method for rapidly analyzing samples for analytes of interest by an homogeneous immunofluorescence assay. The apparatus includes a sample test cartridge having a high control sample section, a low control sample section, and at least one test sample section. Each of these sections contain at least one pre-loaded reagent housed in a well within the cartridge wherein the low control sample section contains a known low amount of an analyte of interest and the high control sample section contains a known high amount of an analyte of interest. The cartridge includes a biosensor comprising a planar waveguide having first and second parallel plane surfaces and an edge extending between them, the edge having a receiving region for receiving a light beam. Each of the high control sample section, the low control sample section, and the test sample control sections have a well which includes a waveguide surface, wherein the contents of each section contacts capture molecules immobilized on the waveguide surface. The capture molecules are configured to specifically bind a chosen analyte and fluoresce when interacting with light passing through the waveguide surface. The concentration of said analyte of interest in said sample fluid is determined by a comparison of intensities of fluorescence of between said capture molecule areas of said sample capture molecule well, said low control capture molecule well, and said high control capture molecule well.

37 Claims, 9 Drawing Sheets

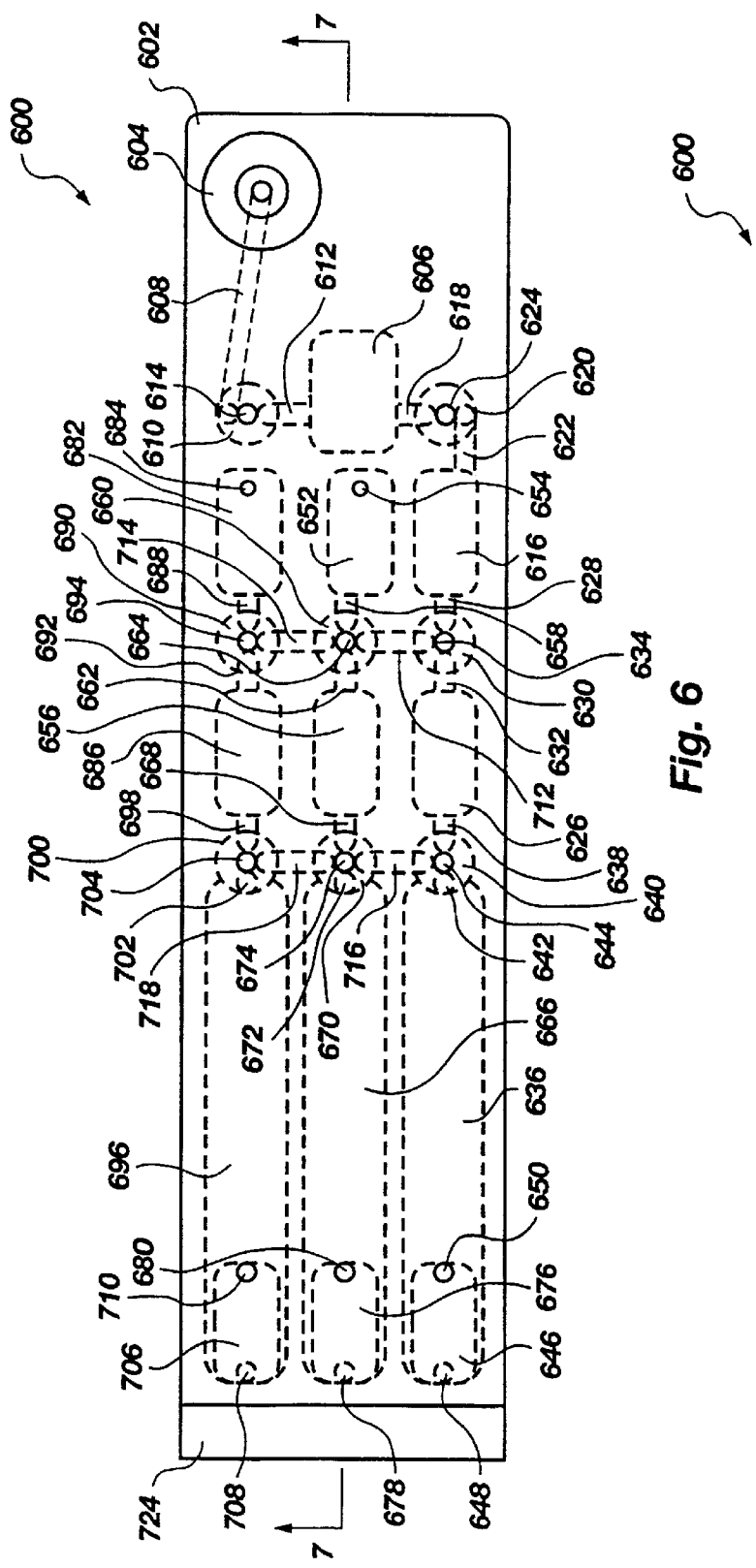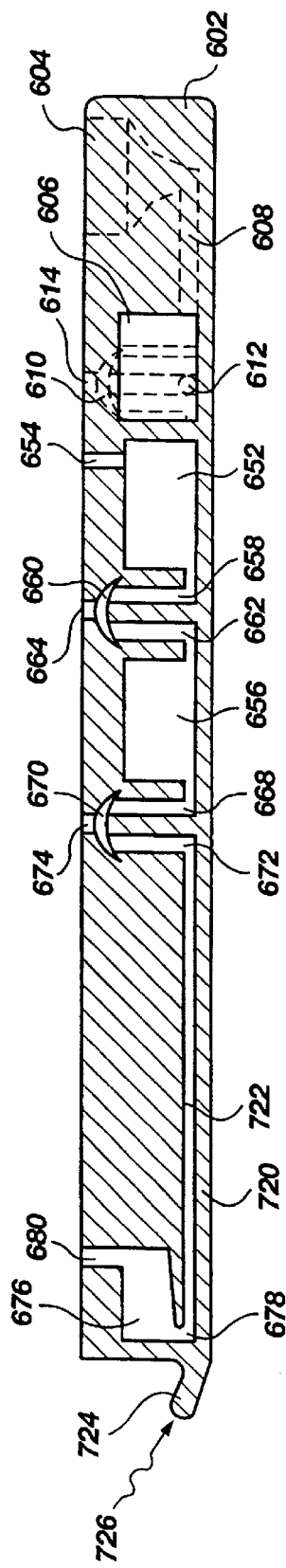

OSCILLATION APPARATUS AND METHODS FOR MULTI-ANALYTE HOMOGENEOUS FLUORO-IMMUNOASSAYS

This is the U.S. National Stage Application of PCT/US97/04378 filed Mar. 19, 1997, also claiming priority to Prov. Application 60/014,713 filed Mar. 19, 1996.

TECHNICAL FIELD

This invention relates to an apparatus and method for rapidly analyzing samples for analytes of interest, and more particularly to a sample test cartridge and associated diagnostic apparatus.

BACKGROUND ART

International Application No. PCT/US94/05567 (Int'l Publ. No. 94/27137, published Nov. 24, 1994) to the University of Utah Research Foundation discloses an apparatus for multi-analyte homogeneous fluoro-immunoassays. The disclosed apparatus uses a planar waveguide (see, e.g., FIGS. 12A, 12B & 13 of Int'l Publ. No. 94/27137).

Biosensor apparatuses based on optical detection of analytes by fluorescence of tracer molecules, have attracted increasing attention in recent years. Such apparatuses are useful for both diagnostic and research purposes. In particular, biosensors for a solid-phase fluoro-immunoassay, in which an antibody or antibody fragment specific to the desired analyte is immobilized on a substrate, and binding of the analyte to the antibody results either directly or indirectly (for example, by means of a labeled tracer) in a fluorescence signal, are becoming an important class of optical biosensor.

In most solid-phase fluoro-immunoassays, to achieve adequate sensitivity, a "wash" step is required to remove unbound tracer before measuring the fluorescence. This problem is particularly true for detection of analytes present at concentrations below nanomolar, as is the case for many analytes of interest in body fluids including blood, serum and urine. However, the wash step is tedious, and care on the part of the technician is required to produce repeatable and accurate results. This problem was overcome in Int'l Publ. No. 94/27137 by providing a fluoro-immunoassay system in which sensitivity to analyte concentrations of $10^{-10}$ to $10^{-13}$ molar or below is achieved without a wash step.

The optical technique discussed in Int'l Publ. No. 94/27137 is known as total internal reflection (abbreviated "TIR"). Evanescent light is light produced when a light beam traveling in a waveguide is totally internally reflected at the interface between the waveguide and a surrounding medium having a lower refractive index. A portion of the electromagnetic field of the internally reflected light penetrates into the surrounding medium and constitutes the evanescent light field.

The intensity of evanescent light drops off exponentially with distance from the waveguide surface. In a fluoro-immunoassay, evanescent light can be used to selectively excite tracer molecules directly or indirectly bound to an immobilized binding agent, while tracer molecules free in solution beyond the evanescent penetration distance are not excited and thus do not contribute "background" fluorescence. The use of evanescent field properties for fluorescence measurements is sometimes referred to as "evanescent sensing." For a glass or a similar silica-based material, or an optical plastic such as polystyrene, with the surrounding medium being an aqueous solution, the region of effective excitation by evanescent light generally extends about 1000 to 2000 Å (angstroms) from the waveguide surface. This depth is sufficient to excite most of the tracer molecules bound to the capture molecules (antibodies, receptor molecules, and the like, or fragments thereof) on the waveguide surface, without exciting the bulk of the tracer molecules that remain free in solution. The fluorescence thus resulting reflects the amount of tracer bound to the immobilized capture molecules, and in turn the amount of analyte present.

The maximum solution depth for efficient evanescent collection by the waveguide approximates the depth of the region of evanescent penetration into the solution, and thus the waveguide-penetrating portion of the tracer fluorescence can also be used to selectively measure fluorescence from tracer bound to the waveguide surface.

U.S. Pat. Nos. RE 33,064 to Carter, 5,081,012 to Flanagan et al., 4,880,752 to Keck, 5,166,515 to Attridge, and 5,156,976 to Slovacek and Love, and EP publication Nos. 0 517 516 and 0 519 623, both by Slovacek et al., all disclose apparatus for fluoro-immunoassays utilizing evanescent sensing principles.

It is desirable for speed and convenience in "routine" testing, for example testing of blood samples for viral antibodies, to have an evanescent immuno-fluorescent biosensor which is disposable and which provides multi-sample measurement capability. Multi-sample capability would allow at least one test sample, a high control sample (such as a sample pre-loaded with a high concentration of analyte molecules of interest), and a low control sample (such as a blank) to be simultaneously illuminated and measured. Simultaneous multi-sample capability would also speed up the process of analyzing multiple samples and would reduce the effects of variation in the level of exciting light which are known to occur with typical light sources. It is also desirable for a medical practitioner to be able to perform a fluoro-immunoassay in his or her office without having to send the samples to a laboratory.

Thus, a need remains for an evanescent biosensor system which provides the desired sensitivity in a fluoro-immunoassay which can be performed inexpensively and quickly by relatively non-skilled persons.

DISCLOSURE OF INVENTION

The invention includes a system having both apparatus and methods for a homogeneous immunofluorescence assay based on evanescent light principles, capable of detecting one or more analytes at concentrations less than pico-molar inexpensively and quickly by non-skilled persons. The overall configuration of the apparatus is preferably a self-contained, small "footprint" assay device 1300, as shown in FIG. 13. The assay device 1300 is specifically designed to be compact and relatively inexpensive for use by a medical practitioner, who may lack technical immunoassay skills in his or her office. The assay device 1300 includes one or more assay cartridges 1302 which are inserted in a cartridge holder 1304 within the assay device housing 1306.

As more thoroughly described herein, the cartridges 1302 have a low control sample section, at least one test sample section, and, preferably, a high control sample section. Each of these sections contains at least one pre-loaded reagent housed in a well within the cartridge 1302. For performing an assay, the medical practitioner needs only deposit the test sample in a sample cup disposed in an appropriate cartridge, and insert the cartridge 1302 into the cartridge holder 1304.

The cartridge 1302 includes a biosensor comprising a planar waveguide having first and second parallel plane surfaces and an edge extending between them, the edge having a receiving region for receiving light to be internally propagated. A semi-cylindrical lens (or its equivalent) is optically adapted to the waveguide adjacent the receiving region of the cartridge 1302.

At least one of the waveguide surfaces has a plurality of capture molecules immobilized thereon. Each of the high control sample section, the low control sample section, and the test sample control sections have an associated well which includes the waveguide surface, wherein the contents of each section contacts the capture molecules. The wells may be associated with means for preventing spillage, such as a membrane, one-way valve, etc. The capture molecules are configured to specifically bind a chosen analyte. The capture molecules may include a plurality of species each specific for a different analyte, and different species may be localized in different and mutually exclusive regions on the waveguide surface.

The assay device housing 1306 utilizes a light source configured and disposed to deliver a sheet beam of light into the waveguide through a receiving region on the cartridge semi-cylindrical lens which generates an evanescent field proximate to the waveguide. The capture molecules have fluorescence-emitting tracer molecules bound thereto, such that the fluorescence-emitting tracer molecules are excited by an evanescent field penetrating into the adjacent solution from a light beam propagated within the waveguide, the propagated beam being introduced at an end or edge of the waveguide.

The assay device housing 1306 also includes a detection means disposed internally for direct collection of the fluorescence from the evanescent zone, direct collection being defined as not requiring penetration of the fluorescence into the waveguide. The detection means is desirably an imaging detector configured to simultaneously separately collect a plurality of fluorescence signals each originating from a different region on the waveguide surface. Thus, the emitted fluorescence is directly collected from the zone of evanescent penetration, not from an edge or end of the waveguide. The imaging detector includes a plurality of photodetection elements spaced from each other in the displaced parallel plane, and a lens (or equivalent means) positioned to focus each of the fluorescence signals onto a respective one of the photodetection elements.

The assay device housing 1306 also includes an internal pump (or equivalent means) which couples with ports disposed on the cartridge 1302 when the cartridge 1302 is inserted into the cartridge holder 1304. The pump supplies positive pressure, vacuum, or atmospheric pressure to a plurality of valves disposed within the cartridges 1302. The valves, in turn, are used by the assay device 1300 to shift the reagents and samples to appropriate chambers within the cartridge 1302. The pump further includes means for oscillating the reagents and samples back and forth across the waveguide surface (having the capture molecules) to induce turbulent flow which increases the performance of the assay.

BRIEF DESCRIPTION OF DRAWINGS

In the drawings, which depict presently preferred embodiment of the invention and in which like reference numerals refer to like parts in different views:

FIG. 6 is a top plan view of a multiple reagent well cartridge of the invention;

FIG. 7 is a side cross-sectional view of the multiple well cartridge of the invention along section line 7—7 of FIG. 6;

BEST MODE FOR CARRYING OUT THE INVENTION

Figure 1:
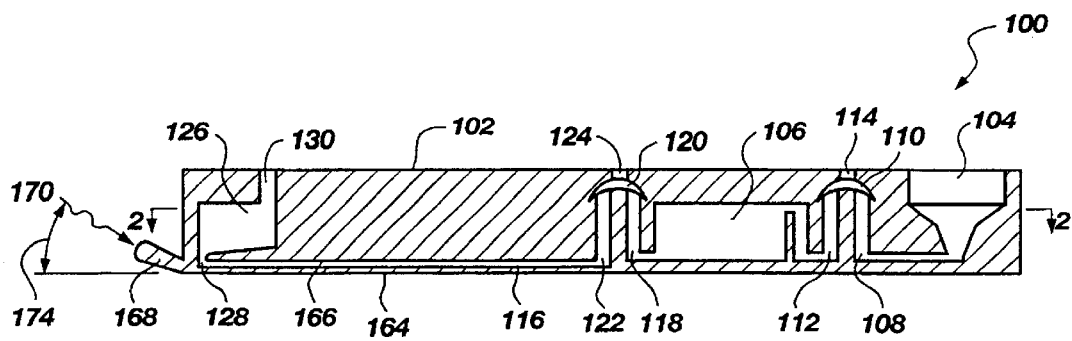
FIG. 1 is a side cross-sectional view of a cartridge according to the invention.
Figure 2:
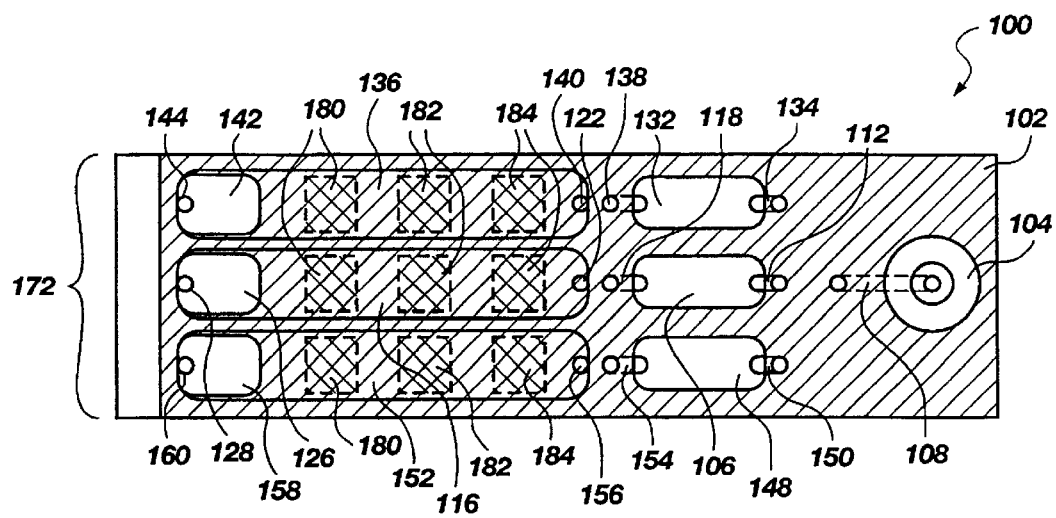
FIG. 2 is a top cross-sectional view of an embodiment of the cartridge of the invention along section lines 2—2 of FIG. 1.

FIG. 1 illustrates a side cross-sectional view of a presently preferred cartridge 100 for use with the invention. FIG. 2 illustrates a top cross-sectional view of an embodiment of the cartridge 100 of the present invention along lines 2—2 of FIG. 1. The cartridge 100 comprises a housing 102 having a sample cup 104 and a sample reagent well 106. The sample cup 104 and the sample reagent well 106 are in fluid communication with one another via a sample cup outlet 108 which extends from the sample cup 104 to a sample cup/sample reagent well valve 110, preferably a hydrophobic membrane valve. The sample cup/sample reagent well valve 110 connects to a sample reagent well inlet 112 which extends into the sample reagent well 106. The sample cup/sample reagent well valve 110 is also in fluid communication with a sample first port 114 which is connected to an external air mechanism, such as a pressure/vacuum pump (not shown). The pressure/vacuum pumps used in the present invention are preferably ASF pumps such as those produced by Pneutronics a division of Parker-Hannifin Corp., Hollis, N.H., US. A pressure/vacuum pump preferably has a series of solenoid valves for regulating air flow to the cartridge. The air flow is used to open and close hydrophobic membrane valves, such as a sample cup/sample reagent well valve 110, and to exert pressure or vacuum on the fluids within the cartridge 100 or vent to the atmosphere.

The sample reagent well 106 is in fluid communication with a sample antibody well 116 via a sample reagent well outlet 118 which extends from the sample reagent well 106 to a sample reagent/sample antibody well valve 120. The sample reagent/sample antibody well valve 120 connects to a sample antibody well inlet 122. The sample reagent/sample antibody well valve 120 is also in fluid communication with a sample second port 124 which is connected to an external air mechanism, such as a pressure/vacuum pump (not shown).

Optionally, the sample antibody well 116 is in fluid communication with a sample oscillation well 126 via a sample oscillation/sample antibody well port 128. The sample oscillation well 126 is also in fluid communication with a sample third port 130 which is connected to an external air mechanism, such as a pressure/vacuum pump (not shown).

The cartridge 100 further includes a low control reagent well 132 which is in fluid communication with a low control first port (not shown, but similar to the sample first port 114) which is connected to an external air mechanism, such as a pressure/vacuum pump (not shown) via a low control reagent well inlet 134 and a low control reagent well valve (not shown, but similar to the sample cup/sample reagent well valve 110). The low control reagent well 132 is also in fluid communication with a low control antibody well 136 via a low control reagent well outlet 138 which extends from the low control reagent well 132 to a low control reagent/low control antibody well valve (not shown, but similar to the sample reagent/sample antibody well valve 120). The low control reagent/low control antibody well valve (not shown) connects to a low control antibody well inlet 140. The low control reagent/low control antibody well valve (not shown) is also in fluid communication with a low control second port (not shown, but similar to sample second port 124) which is connected to an external air mechanism, such as a pressure/vacuum pump (not shown).

Optionally, the low control antibody well 136 is in fluid communication with a low control oscillation well 142 via a low control oscillation/low control antibody well port 144. The low control oscillation well 142 is also in fluid communication with a low control third port (not shown, but similar to sample third port 130) which is connected to an external air mechanism, such as a pressure/vacuum pump (not shown).

The cartridge 100 further includes a high control reagent well 148 which is in fluid communication with a high control first port (not shown, but similar to sample first port 114) which is connected to an external air mechanism, such as a pressure/vacuum pump (not shown) via a high control reagent well inlet 150 and a high control reagent well valve (not shown, but similar to the sample cup/sample reagent well valve 110). The high control reagent well 148 is also in fluid communication with a high control antibody well 152 via a high control reagent well outlet 154 which extends from the high control reagent well 148 to a high control reagent/high control antibody well valve (not shown, but similar to the sample reagent/sample antibody well valve 120). The high control reagent/high control antibody well valve (not shown) connects to a high control antibody well inlet 156. The high control reagent/high control antibody well valve (not shown) is also in fluid communication with a high control second port (not shown, but similar to sample second port 124) which is connected to an external air mechanism, such as a pressure/vacuum pump (not shown).

Optionally, the high control antibody well 152 is in fluid communication with a high control oscillation well 158 via a high control oscillation/high control antibody well port 160. The high control oscillation well 158 is also in fluid communication with a high control third port (not shown, but similar to sample third port 130) which is connected to an external air mechanism, such as a pressure/vacuum pump (not shown).

The sample antibody well 116, the low control antibody well 136, and the high control antibody well 152 each include a waveguide 164 as a lower wall and an upper wall surface 166 (shown only on the sample antibody well 116). The antibody well upper wall surface 166 is preferably made of a light absorbing (e.g. opaque) material. The waveguide 164 is preferably planar to form the lower wall of each the sample antibody well 116, the low control antibody well 136, and the high control antibody well 152. The waveguide 164 is preferably made of an optical plastic as polystyrene, polymethylacrylate ("PMMA"), polycarbonate, or the like having a refractive index greater than 1.33 (the index of water being 1.33). In one embodiment (not shown), the waveguide 164 is made of a laminate of plastics, one serving as a structural substrate, and the other serving to transmit the light.

The waveguide 164 includes an angled integral lens 168 configured to accept an angled beam 170 from a light source (not shown). For this purpose, the angled beam 170 preferably originates from a laser (not shown) such as an argon ion laser or a laser diode capable of emitting at center wavelengths of between about 488 and 514.5 nanometers ("nm") and between about 600 and 900 nm, respectively. The angled beam 170 should be shaped to a sheet of width approximating the width of a receiving region 172 of the waveguide 164, and of relatively narrow thickness (preferable between 25%–90% of the thickness of the angled integral lens 168), using cylindrical and/or spherical lenses as known in the art.

The angled beam 170 which enters the angled integral lens 168 is angled so as to increase, for a given power of the input laser beam, the surface power density (i.e., intensity) of the evanescent field which forms over the waveguide 164 within the sample antibody well 116. Desirably, the angles of all of the laser light after having passed through angled integral lens 168 is selected to be less than, but near the critical angle of the waveguide/solution interface (not shown). The closer the mean beam entry angle 174 is to this critical angle, the greater the increase in evanescent intensity. However, if the mean beam entry angle 174 is too near the critical angle, it could result in some of the entering light escaping at the waveguide/solution interface 550 (shown in FIG. 5), thus dramatically increasing fluorescence of the unbound labels in the bulk solution. Thus, there is an optimum angle that can be determined experimentally. Generally, a mean beam entry angle 174 of a few degrees less than the critical angle (from about 5 to about 15 degrees less), will be useful.

For a transparent (e.g., crystal) polystyrene waveguide, the critical angle is about 33°, and the presently preferred beam entry angle is between about 15 and 25°; with these values, an increase in evanescent light intensity of at least about a factor of two is achieved over using a nominal 0° beam entry angle.

Figure 3:
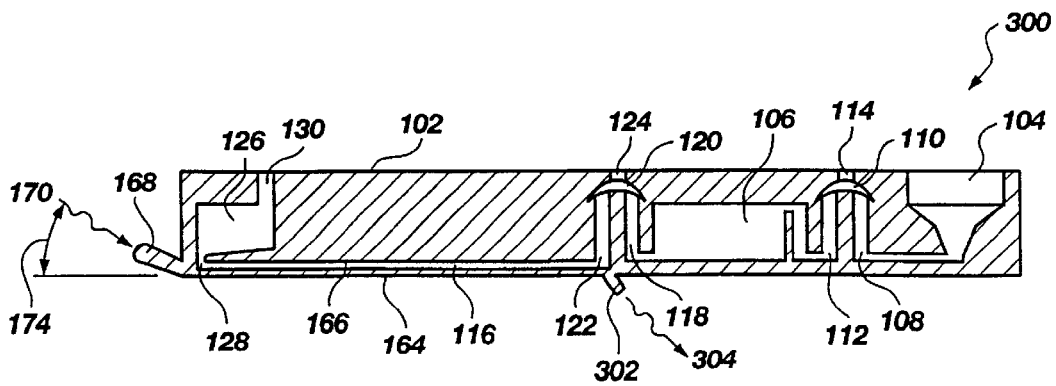
FIG. 3 is a side cross-sectional view of an alternate embodiment of a cartridge according to the invention.

FIG. 3 is a side cross-sectional view of an alternate cartridge 300 of the present invention. The alternate cartridge 300 is very similar to the cartridge 100, therefore components common to FIG. 1 and FIG. 3 retain the same numeric designation. The alternate cartridge 300 differs from the cartridge 100 in that the waveguide 164 has an output lens 302 near the antibody well inlets 122, 140, and 156 of the antibody wells 116, 136, and 152 of FIG. 2, respectively. The output lens 302 is present to ensure that output light 304 is detected. Unlike the end collection of light from a lens described in U.S. Pat. No. 4,582,809 to Block et al. (Apr. 15, 1986), in the present invention, the output light 304 may be detected at the end of the output lens 302 for two reasons. The first reason is as a quality control measure. The angled beam 170 passing through the waveguide 164 to the output lens 302 may be measured so that the operator of an apparatus using the cartridge 300 knows that the cartridge 300 has been properly placed in the apparatus and that the light source is still working.

Alternatively, the diagnostic apparatus could be set to first detect a predetermined strength of output light 304 at the end of the output lens 302, before the apparatus will operate, again to ensure that the cartridge 300 has been properly placed. The second reason for end detection involves the calibration of the apparatus to ensure that the amount of light traveling through the waveguide 164 is uniform, and if it is not uniform to accommodate any differences.

The cartridge 100 can be molded by any known industry standard molding technique, such as injection molding. However, the waveguide 164 must be transparent and of high optical quality which is difficult to achieve when molding the waveguide 164 as part of a larger apparatus, such as the cartridge 100. Furthermore, the upper wall surfaces of the sample antibody well 116, the low control antibody well 136, and the high control antibody well 152 is preferably made of a light absorbing (opaque) material. It may be difficult to form the absorbing material upper wall surface simultaneously with the formation of the transparent waveguide. Moreover, it would be difficult to mold the valving system within the cartridge 100. Therefore, it is preferable to form the cartridge 100 in modular pieces.

Figure 4:
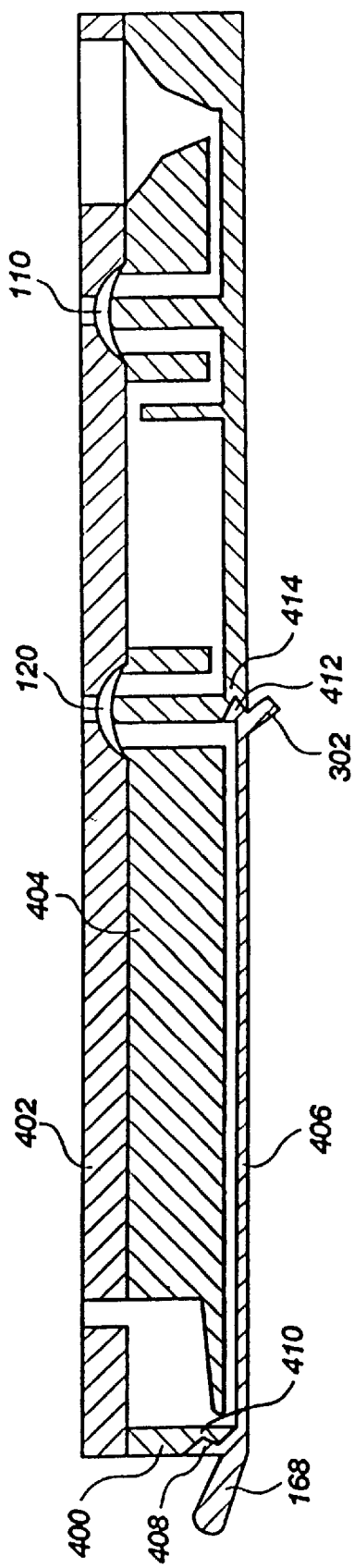
FIG. 4 is a side cross-sectional view of a modular embodiment of a cartridge according to the invention.

FIG. 4 illustrates a side cross-sectional view of a modular cartridge 400 of the present invention. The modular cartridge 400 comprises an upper portion 402, a lower portion 404, and a detachable waveguide 406. The intersection of the upper cartridge portion 402 and the lower cartridge portion 404 coincides with the position of the valving mechanisms (e.g., the sample cup/sample reagent well valve 110, the sample reagent/sample antibody well valve 120, etc.). Thus, the valving mechanisms can be inserted into place prior to the attachment of the upper cartridge portion 402 and the lower cartridge portion 404. The upper cartridge portion 402 and the lower cartridge portion 404 may be bonded together with an appropriate adhesive or via thermal bonding. The detachable waveguide 406 preferably has a forward clip 408 proximate the angled integral lens 168 which mates with a forward clip recess 410 formed in the lower cartridge portion 404. The detachable waveguide 406 further includes a rear clip 412 proximate the output lens 302 which mates with a rear clip recess 414 formed in the lower cartridge portion 404. The forward clip 408 and the rear clip 412 when mated with the forward clip recess 410 and the rear clip recess 414 detachably attaches the detachable waveguide 406 to the lower cartridge portion 404.

Figure 5:
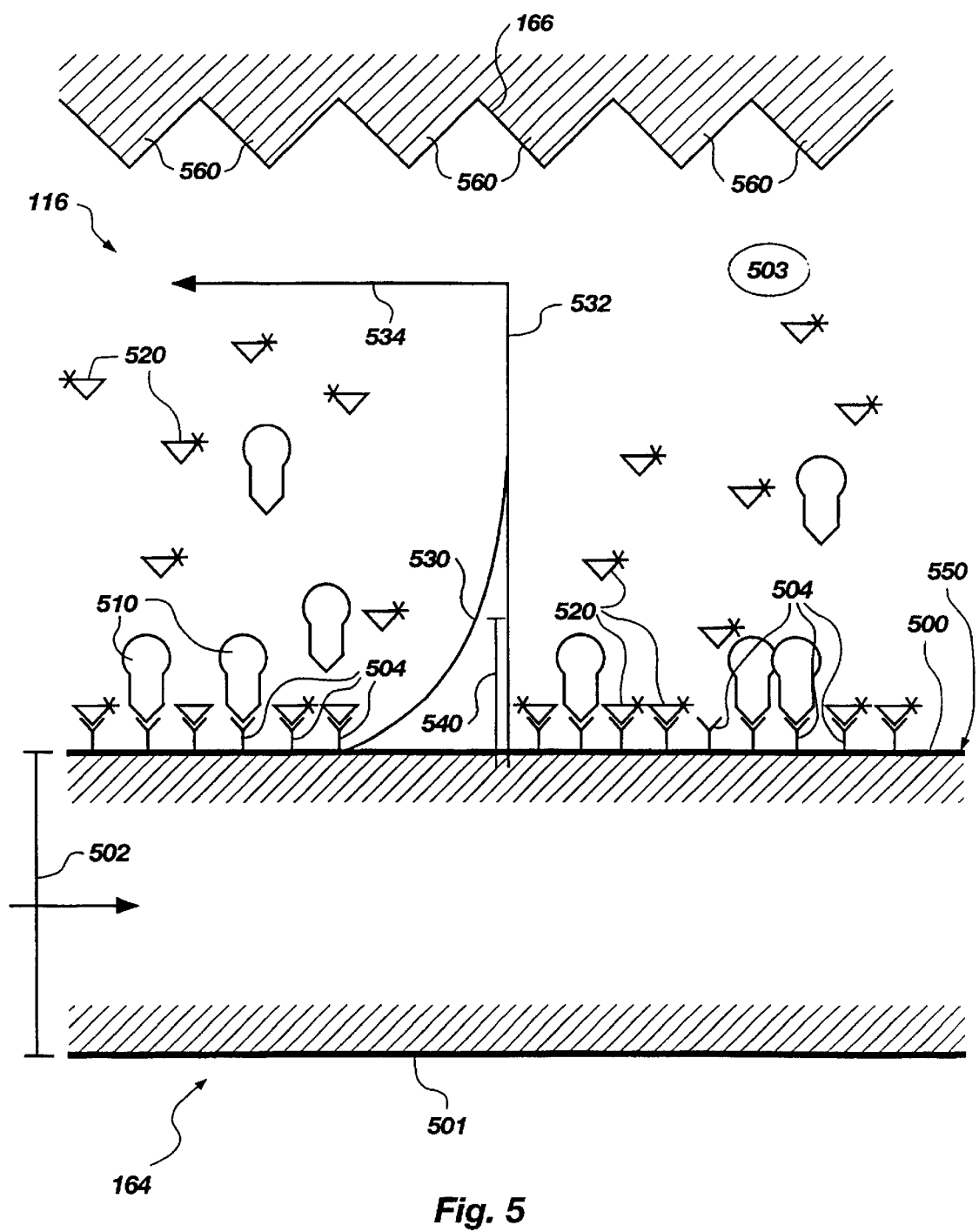
FIG. 5 is a stylized, side cross-sectional view of a portion of the waveguide and the biochemical components of a competition immunofluorescent assay according to the invention.

An exemplary assay is generally carried out as illustrated in FIG. 5. The waveguide 164 has at least one planar surface 500 spaced from a second surface 501 by a width 502. At least one planar surface 500 is disposed in contact with a sample solution 503. A plurality of capture molecules 504 are immobilized on surface 500. The sample solution contains a plurality of analyte molecules 510 of a selected analyte, and a plurality of tracer molecules 520. The capture molecules 504 are chosen or constructed to bind to a binding moiety present on each of the analyte molecules 510. The tracer molecule 520 is chosen or constructed to emit fluorescent light in response to stimulation by light of the appropriate wavelength, such as an argon laser or a laser diode capable of emitting at center wavelengths of between about 488 and 514.5 nanometers ("nm") and between about 600 and 900 nm, respectively, as previously discussed. The level of fluorescence emitted by the tracer molecules 520 is a measure of the amount of analyte bound to the capture molecule and is thereby reflective of the concentration of analyte molecules 510 in the solution.

When light is being propagated in the waveguide 164 and internally reflected at the surfaces 500, 501, an evanescent light field is produced having an intensity curve 530 which drops off with distance from the planar surface 500, as diagramed relative to a distance axis 532. An excitation zone 540 is the only region of the solution in which the evanescent light intensity is sufficient to excite a significant or detectable fraction of the tracer molecules 520 (not to scale). The tracer molecules 520 outside the excitation zone 540 will contribute little or no induced fluorescence. The excitation zone 540 is typically between about 1000 and 2000 Å in depth.

Capture molecules 504 are reactive with the analyte molecules 510, and may be whole antibodies, antibody fragments such as Fab' fragments, peptides, epitopes, membrane receptors, whole antigenic molecules (haptens) or antigenic fragments, oligopeptides, oligonucleutides, mimitopes, nucleic acids and/or mixtures thereof. Capture molecules 504 may also be a receptor molecule of the kind usually found on a cell or organelle membrane and which has specificity for a desired analyte, or a portion thereof carrying the analyte-specific-binding property of the receptor.

In FIG. 5, a competition assay scheme is depicted (also termed a displacement assay). However, as will be apparent to the skilled person, alternate assay schemes such as sandwich assays may be performed with the present apparatus. See, e.g. U.S. Pat. Nos. 4,376,110 and 4,486,530 to Hybritech, Inc.

The capture molecules 504 may be immobilized on the surface 500 by any method known in the art. However, in the preferred embodiment, the capture molecules are immobilized in a site-specific manner. As used in this application, the term "site-specific" means that specific sites on the capture molecules are involved in the coupling to the waveguide, rather than random sites as with typical prior art methods. Int'l Publ. No. 94/27137, which has been previously referenced, details methods for site-specific immobilization of capture molecules to the surface of the optical substrate by means of a protein-resistant coating on the substrate.

As previously stated, the intensity of evanescent light drops off rapidly with distance from the waveguide surface. Thus, only the tracer molecules 520 which are within the effective excitation range 540 (not necessarily to scale) from the planar surface 500, will be excited by the evanescent light to emit fluorescence. The excitation range 540 is generally about 1000 to 2000 Å. This range is sufficient to ensure that essentially all tracer molecules 520 which are bound (directly or indirectly) to capture molecules 504 will be detected, while the bulk of the tracer molecules which remain free in solution are outside the effective excitation range. Measurements of fluorescence are made by spectroscopy. Fluorescence detection by a light detector may be achieved with either a monochromator or a bandpass filter in conjunction with a charge-coupled device (abbreviated "CCD"), a photomultiplier, a semiconductor photodiode, or an array of such detectors (not shown) directed toward the second surface 501.

In the embodiment of FIG. 5, the immunoassay is a competition assay in which the tracer molecules 520 are constructed such that the capture molecules 504 will bind the tracer molecules 520 in place of the analyte molecules 510. Higher concentrations of analyte molecules 510 will cause most of the tracer molecules 520 to be displaced into the surrounding solution from the capture molecules 504, thus reducing the number of tracer molecules within the excitation range 540. This reduced binding of tracer molecules, in turn, reduces the amount of fluorescence. In contrast, the lower concentrations of the analyte molecules 510 will allow the tracer molecules 520 to bind to the capture molecules 504, and thus to be held within the excitation range 540.

Referring to FIG. 2, the waveguide 164 has patches 180, 182, and 184 disposed thereon within the high control antibody well 152, the sample antibody well 116, and the low control antibody well 136. The patches 180, 182, and 184 should be spaced appropriately to correspond to the positioning of the light detector or element of the light detector, such as photodiodes or pixels of a CCD camera. These patches 180, 182, and 184 each comprise a different immobilized Fab' species or the like. Thus, each patch set (i.e., 180, 182, and 184) can detect different analyte molecules of interest.

FIG. 6 illustrates a top view of an embodiment of a multiple reagent well cartridge 600 of the present invention. FIG. 7 illustrates a side cross sectional view of an embodiment of the multiple reagent well cartridge 600 of the present invention along lines 7—7 of FIG. 6. The cartridge 600 comprises a housing 602 having a sample cup 604 and a sample waste well 606. The sample cup 604 and the sample waste well 606 are in fluid communication via a sample cup outlet 608 which extends from the sample cup 604 to a sample cup/sample waste well valve 610. The sample cup/sample waste well valve 610 connects to a sample waste well inlet 612 which extends into the sample waste well 606. The sample cup/sample waste well valve 610 is also in fluid communication with a sample first port 614 which is connected to an external air mechanism, such as a pressure/vacuum pump (not shown).

The sample waste well 606 is in fluid communication with a first sample reagent well 616 via a sample waste well outlet 618 which extends from the sample waste well 606 to a sample waste/first sample reagent well valve 620. The sample waste/first sample reagent well valve 620 connects to a first sample reagent well inlet 622. The sample waste/first sample reagent well valve 620 is also in fluid communication with a sample second port 624 which is connected to an external air mechanism, such as a pressure/vacuum pump (not shown).

The first sample reagent well 616 is in fluid communication with a second sample reagent well 626 via a sample reagent well outlet 628 which extends from the first sample reagent well 616 to a first sample reagent/second sample reagent well valve 630. The first sample reagent/second sample reagent well valve 630 connects to a second sample reagent well inlet 632. The first sample reagent/second sample reagent well valve 630 is also in fluid communication with a sample third port 634 which is connected to an external air mechanism, such as a pressure/vacuum pump (not shown).

The second sample reagent well 626 is in fluid communication with a sample antibody well 636 via a second sample reagent well outlet 638 which extends from the second sample reagent well 626 to a second sample reagent/sample antibody well valve 640. The second sample reagent/sample antibody well valve 640 connects to a sample antibody well inlet 642. The second sample reagent/sample antibody well valve 640 is also in fluid communication with a sample fourth port 644 which is connected to an external air mechanism, such as a pressure/vacuum pump (not shown).

Optionally, the sample antibody well 636 is in fluid communication with a sample oscillation well 646 via a sample oscillation/sample antibody well port 648. The sample oscillation well 646 is also in fluid communication with a sample fifth port 650 which is connected to an external air mechanism, such as a pressure/vacuum pump (not shown).

The cartridge 600 further includes a first low control reagent well 652 which is in fluid communication with a low control first port 654 which is connected to an external air mechanism, such as a pressure/vacuum pump (not shown). The first low control reagent well 652 is also in fluid communication with a second low control reagent well 656 via a first low control reagent well outlet 658 which extends from the first low control reagent well 652 to a first low control reagent/second low control reagent well valve 660. The first low control reagent/second low control reagent well valve 660 connects to a second low control reagent well inlet 662. The first low control reagent/second low control reagent well valve 660 is also in fluid communication with a low control second port 664 which is connected to an external air mechanism, such as a pressure/vacuum pump (not shown).

The second low control reagent well 656 is also in fluid communication with a low control antibody well 666 via a low control reagent well outlet 668 which extends from the second low control reagent well 656 to a second low control reagent/low control antibody well valve 670. The second low control reagent/low control antibody well valve 670 connects to a low control antibody well inlet 672. The second low control reagent/low control antibody well valve 670 is also in fluid communication with a low control third port 674 which is connected to an external air mechanism, such as a pressure/vacuum pump (not shown).

Optionally, the low control antibody well 666 is in fluid communication with a low control oscillation well 676 via a low control oscillation/low control antibody well port 678. The low control oscillation well 676 is also in fluid communication with a low control fourth port 680 which is connected to an external air mechanism, such as a pressure/vacuum pump (not shown).

The cartridge 600 further includes a first high control reagent well 682 which is in fluid communication with a high control first port 684 which is connected to an external air mechanism, such as a pressure/vacuum pump (not shown). The first high control reagent well 682 is also in fluid communication with a second high control reagent well 686 via a first high control reagent well outlet 688 which extends from the first high control reagent well 682 to a first high control reagent/second high control reagent well valve 690. The first high control reagent/second high control reagent well valve 690 connects to a second high control reagent well inlet 692. The first high control reagent/second high control reagent well valve 690 is also in fluid communication with a high control second port 694 which is connected to an external air mechanism, such as a pressure/vacuum pump (not shown).

The second high control reagent well 686 is also in fluid communication with a high control antibody well 696 via a high control reagent well outlet 698 which extends from the second high control reagent well 686 to a second high control reagent/high control antibody well valve 700. The second high control reagent/high control antibody well valve 700 connects to a high control antibody well inlet 702. The second high control reagent/high control antibody well valve 700 is also in fluid communication with a high control third port 704 which is connected to an external air mechanism, such as a pressure/vacuum pump (not shown).

Optionally, the high control antibody well 696 is in fluid communication with a high control oscillation well 706 via a high control oscillation/high control antibody well port 708. The high control oscillation well 706 is also in fluid communication with a high control fourth port 710 which is connected to an external air mechanism, such as a pressure/vacuum pump (not shown).

The cartridge 600 optionally includes a first sample reagent/first low control reagent side port 712 for fluid communication between the first sample reagent/second sample reagent well valve 630 and the first low control reagent/second low control reagent well valve 660; a first low control reagent/first high control reagent side port 714 for fluid communication between the first low control reagent/second low control reagent well valve 660 and the first high control reagent/second high control reagent well valve 690; a second sample reagent/second low control reagent side port 716 for fluid communication between the second sample reagent/sample antibody well valve 640 and the second low control reagent/low control antibody well valve 670; and a second low control reagent/second high control reagent side port 718 for fluid communication between the second low control reagent/low control antibody well valve 670 and the second high control reagent/high control antibody well valve 700. These side ports (i.e., 712, 714, 716, and 718) allow the flexibility of being able to transport any fluids within the cartridge 600 between the various wells.

The sample antibody well 636, the low control antibody well 666, and the high control antibody well 696 each include a waveguide 720 as a lower wall and an upper wall surface 722 (shown only on the low control antibody well 666). The antibody well upper wall surface 722 is preferably made of a light absorbing (opaque) material. The waveguide 720 is preferably planar to form the lower wall of each the sample antibody well 636, the low control antibody well 666, and the high control antibody well 696, as previously described. The waveguide 720 includes an angled integral lens 724 configured to accept an angled beam 726 from a light source (not shown), as previously discussed.

It has been found that by oscillating the solutions within the antibody wells (FIG. 2–116, 136, 152 and FIG. 6–636, 666, 696) the assay performance is increased. Increased assay performance is a result of turbulent flow of the fluid caused by the oscillation. Oscillation within the cartridge can be achieved by alternating the opening and closing of valving of the pressure/vacuum pump or through the use of an additional oscillation mechanism. For example, turbulent flow of the sample solution 503 results in a more efficient capture of the analyte molecules 510 of interest by the capture molecules 504 attached to the planar surface 500 (see FIG. 5). Turbulent flow is particularly important in viscous sample solutions, such as blood, serum, or the like. Such viscous substances restrict the free movement of the components within the sample solution 503. Thus, without a turbulent flow churning the components within the antibody well, the contact of the analyte molecules 510 with the capture molecules 504 would be substantially impaired.

Figure 8:
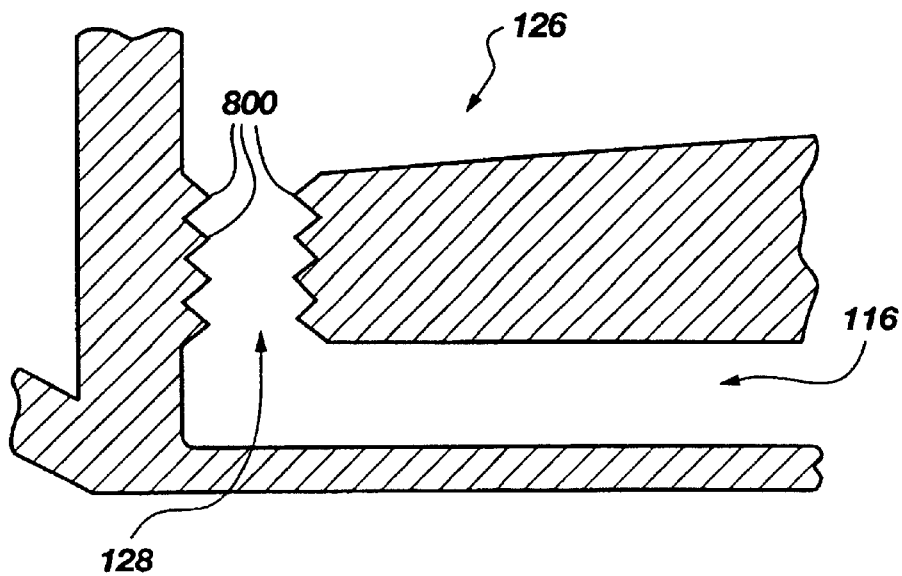
FIG. 8 is a side cross-sectional view of a plurality of baffles within an opening between an oscillation well and an antibody well of the invention.
Figure 9:
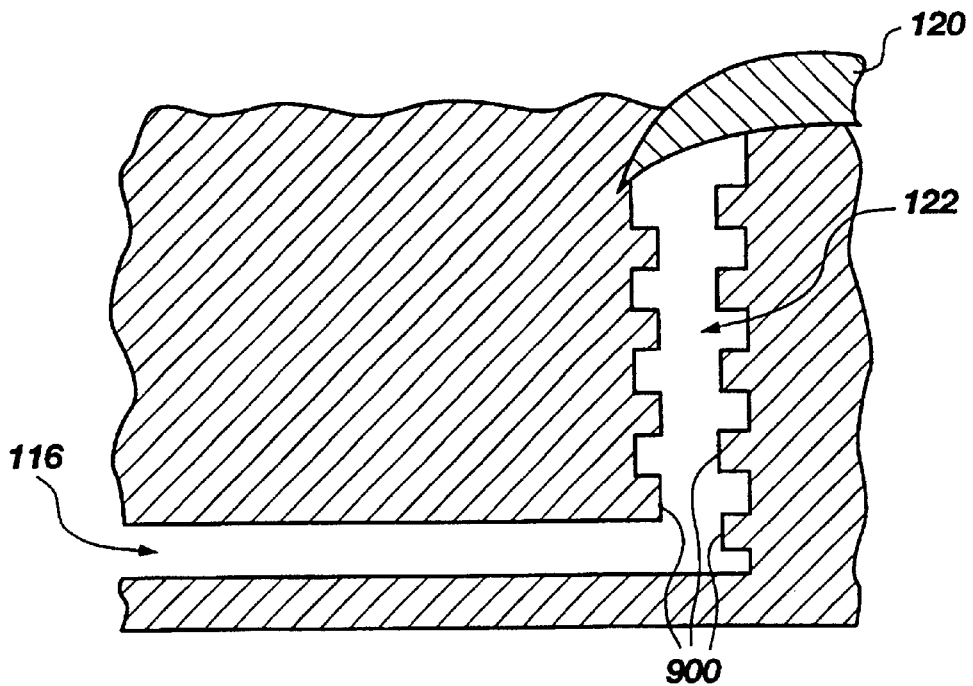
FIG. 9 is a side cross-sectional view of a plurality of baffles within an opening between a reagent/antibody well valve and an antibody well of the invention.

In order to increase the turbulence within the antibody wells, a plurality of baffles 560 (see FIG. 5) may be positioned on the upper wall surfaces 166 of the antibody wells. The baffles 560 may be of any effective length, height and shape, such as square, triangular, or semicircular (in cross-section). Turbulence also may be induced at the opening of the antibody wells. FIG. 8 illustrates a plurality of baffles 800 within the opening between an oscillation well and an antibody well. For example, the baffles 800 are disposed within the sample oscillation/sample antibody well port 128 between the sample oscillation well 126 and the sample antibody well 116, as shown in FIG. 1. FIG. 9 illustrates a plurality of baffles 900 within the opening between a reagent/antibody well valve and an antibody well. For example, the baffles 900 are disposed within the sample oscillation/sample antibody well port 128 between the sample reagent/sample antibody well valve 120 and the antibody well 116, as shown in FIG. 1.

Figure 10:
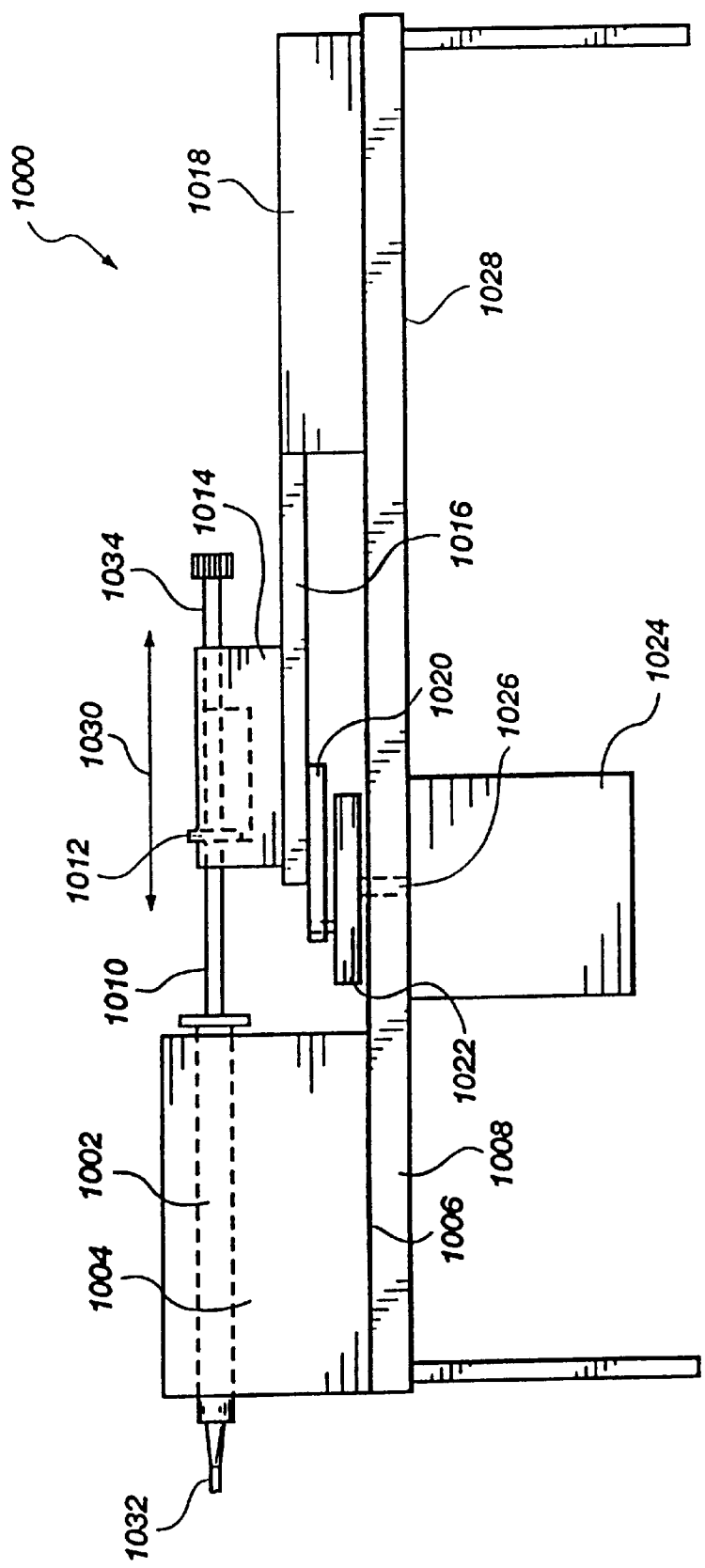
FIG. 10 is a side plan view of a fluid oscillation mechanism of the invention.
Figure 11:
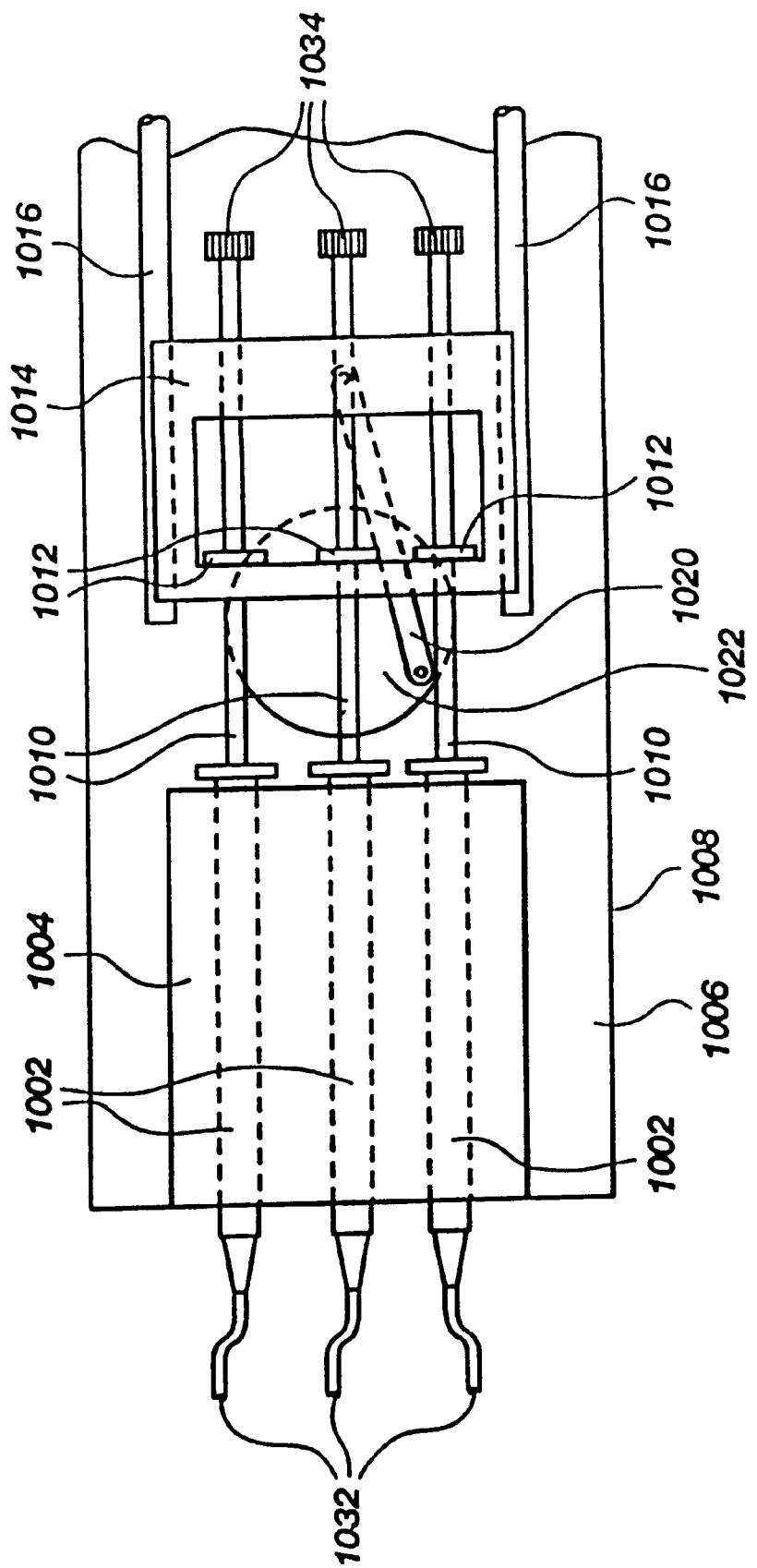
FIG. 11 is a top plan view of a fluid oscillation mechanism of the invention.

FIGS. 10 and 11 illustrate a fluid oscillation mechanism 1000 for oscillating the solution within the antibody wells (FIG. 2–116, 136, 152 and FIG. 6–636, 666, 696). The fluid oscillation mechanism 1000 comprises a plurality of syringes 1002 disposed within a syringe housing 1004 mounted to an upper surface 1006 of a base plate 1008. Each of the syringes 1002 has a syringe plunger 1010. An end 1012 of each of the syringe plungers 1010 is slidably disposed within a movable housing 1014. The movable housing 1014 rests on a pair of slider rods 1016. Preferably, the movable housing 1012 has a series of linear bearings (not shown) which rest on the slider rods 1016. The slider rods 1016 are attached to a slide mechanism 1018 which is mounted to the base plate upper surface 1006.

In the depicted embodiment, a crank 1020 is rotatably attached at one end to the movable housing 1014 and rotatably attached at the other end to a crank wheel 1022. The crank wheel 1022 is supported and rotated by a drive motor 1024 via a drive line 1026. The drive motor 1024 is preferably variable speed low RPM motor. The drive motor 1024 is attached to a lower surface 1028 of the base plate 1008 with the drive line 1026 extending therethrough to the base plate upper surface 1006.

Thus, the fluid oscillation mechanism operates by rotating the motor mechanism (not shown) of the drive motor 1024 which in turn rotates the crank wheel 1022. As the crank wheel 1002 rotates, the crank 1020 pushes and pulls on the movable housing 1014. The movable housing 1014 slides along the slider rods 1016 in a back and forth direction 1030. The movement of the movable housing 1014 slides the syringe plungers 1010 back and forth within the syringes 1002. The back and forth movement of the syringe plungers 1010 causes a pushing and pulling of the air or other fluid within the syringes 1002. This fluid movement within the syringes 1002 is translated to the cartridge (not shown) of the present invention via hoses 1032 attached to the cartridge (not shown) and to the syringes 1002.

The stroke length of the syringe plungers 1010 can be adjusted by a plurality of syringe plunger stroke adjustment screws 1034. The stroke adjustment screws 1034 are threadably attached to the movable housing 1014 and make contact with the syringe plungers 1010.

It is of course understood that the plurality of syringes 1002 could be replaced with a single larger syringe (not shown) or equivalent mechanism wherein the air being pushed and pulled in the syringe is manifolded into an appropriate number of hoses.

It is also understood that the oscillation mechanism 1000 can be used with any flow cell system or the like for performing an assay rather than only the currently disclosed cartridge system.

Figure 12:
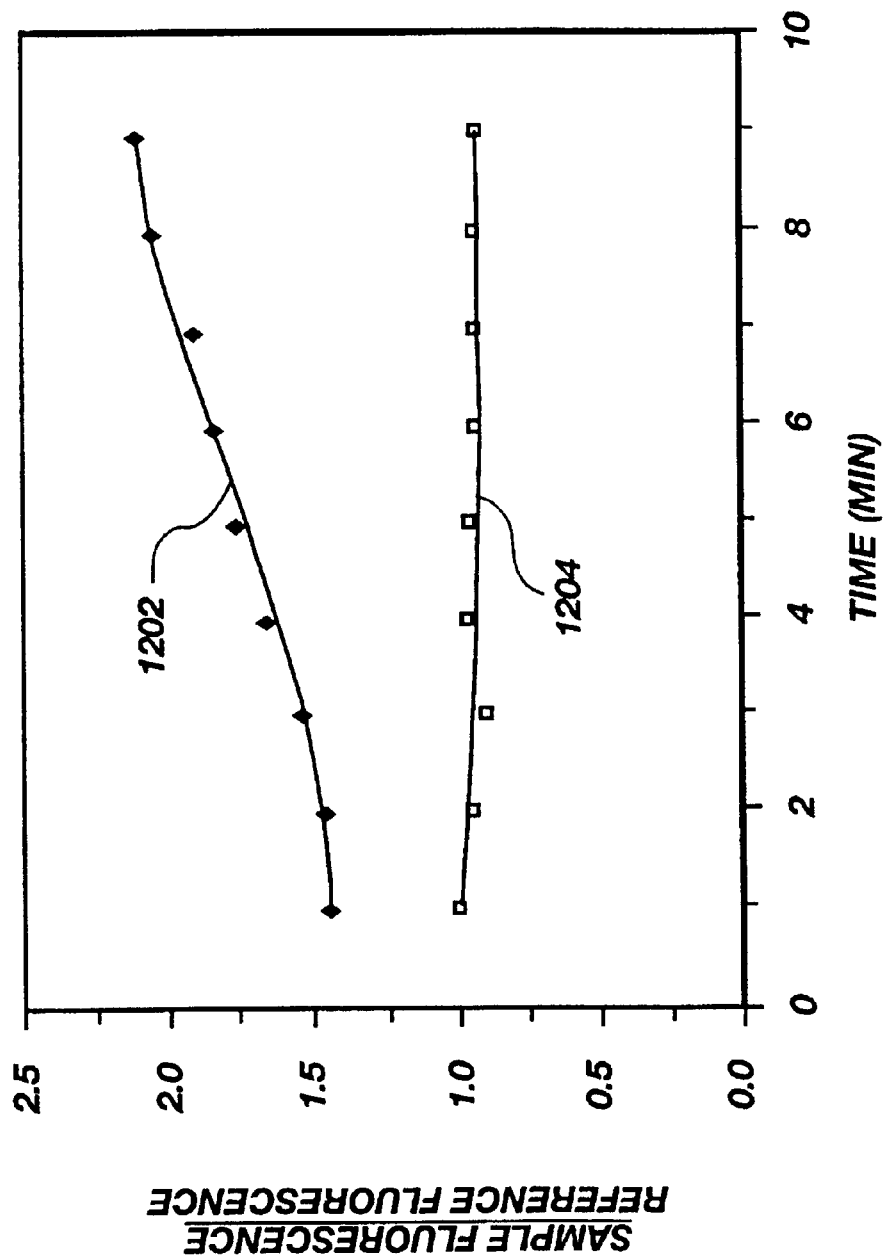
FIG. 12 is a graph depicting a whole blood and plasma CKMB assay with, and without agitation.

An experiment is performed to determine the effect on performance of an assay using oscillation causing turbulence within an antibody well on whole blood ("WB"), 50% whole blood ("50% WB"), and 50% plasma (FIG. 12). First lines represent the ratio of sample fluorescence to reference fluorescent wherein in the CKMB level in the samples in turbulent antibody wells. Second lines represent the ratio of sample fluorescence to reference fluorescence wherein in the CKMB level of the same samples in non-flow condition antibody wells. As can be seen, —oscillation (or agitation) of the samples in the antibody wells greatly increases an assay's sensitivity.

The standard operation of the cartridge 100 as shown in FIGS. 1 and 2 (as well as cartridge 300 in FIG. 3) begins with an operator depositing a predetermined quantity of sample solution into the sample cup 104. The valving system (i.e., valves 110 and 120) draws the sample solution into the sample reagent well 106 which is pre-loaded with an appropriate reagent. The sample mixture and reagent are mixed by shifting the mixture between the sample cup 104 and the reagent well 106 using the valving system. The reagent well 106 may be vented to prevent bubble formation.

Once the sample mixture and reagent are mixed, the mixture is transferred into the sample antibody well 116 and the oscillation well 126. The mixture is then oscillated through the antibody well 116 with an oscillation means, such as alternating the opening and closing of valving of the pressure/vacuum pump or by the oscillation mechanism 1000 illustrated in FIGS. 10 and 11. The hose 1032 (FIGS. 10 and 11) may be attached to either sample first port 114 or sample third port 130 to facilitate the oscillation.

The high control portion (i.e., the reagent well 148, the antibody well 152, and the oscillation well 158) and the low control portion (i.e., the reagent well 132, the antibody well 136, and the oscillation well 142) of the cartridge 100 operate in much the same manner as the sample portion, as described above. However, the high control reagent well 148 is pre-loaded containing a known high concentration of each analyte molecule 510 of interest, and the low control reagent well 132 is also pre-loaded containing no or few analyte molecules 510 of interest. Thus, no mixing step is necessary.

It is of course understood that an alternative operation of the cartridge 100 could begin with an operator depositing a quantity of sample solution above a predetermined minimum amount into the sample cup 104. The valving system (i.e., valves 110 and 120) draws the sample solution into the sample reagent well 106 which is pre-loaded with an appropriate reagent. The filling of the sample reagent well 106 is the proper measure of sample solution for the assay. The mixing of the sample mixture and reagent is achieved during the oscillation through the sample antibody well 116. All other operation steps remain the same.

The standard operation of the cartridge 600 as shown in FIGS. 6 and 7 begins with an operator depositing a quantity of sample solution above a predetermined minimum amount into the sample cup 604. The valving system (i.e., valves 610 and 620) draws the sample solution into the sample waste well 606. The sample solution is then drawn into the first sample reagent well 616, which may contain a first reagent, from the sample waste well 606. The filling of the first sample reagent well 616 is the proper measure of sample solution for the assay. The sample solution/first reagent mixture is drawn into the second sample reagent well 626 which may contain a second reagent. The sample solution/first reagent/second reagent mixture is shifted between the first sample reagent well 616 and the second sample reagent well 626 to mix the sample solution/first reagent/second reagent mixture. The sample solution/first reagent/second reagent mixture is transferred into the sample antibody well 636 and the sample oscillation well 646. The first sample reagent well 616 is vented to avoid bubble formation. The excess sample solution/first reagent/second reagent mixture is drawn into the first sample reagent well 616 and the sample waste well 606, leaving the sample antibody well 636 and the sample oscillation well 646 full, and the second sample reagent well 626 empty. The sample solution/first reagent/second reagent mixture is then oscillated between the sample oscillation well 646 and the second sample reagent well 626 through the sample antibody well 636. If required, the first sample reagent well 616 is vented to avoid bubble formation. If required, the sample oscillation well 646 and the sample antibody well 636 are emptied prior to optical reading the fluorescence.

The high control portion (i.e., the first reagent well 682, the second reagent well 686, the antibody well 696, and the oscillation well 706) and the low control portion (i.e., the first reagent well 652, the second reagent well 656, the antibody well 666, and the oscillation well 676) of the cartridge 600 operate in much the same matter as the sample portion, as described above. However, the first high control reagent well 682 is pre-loaded with a known high concentration of each analyte molecules 510 of interest and possibly a first high control reagent, and the first low control reagent well 652 is also pre-loaded with a reagent containing no or few analyte molecules 510 or no reagent at all.

The concentration of the analyte molecules 510 within the sample solution 503 is determined by a comparison of the intensity of fluorescence within the antibody wells. Referring to FIGS. 1 and 2 for example, the cartridge 100 preferably contains three antibody wells: the sample antibody well 116, the low control antibody well 136, and the high control antibody well 152. As previously discussed, the sample portion of the cartridge contains the sample solution 503 having an unknown concentration of analyte molecules 510 of interest. The low control portion preferably has a "blank" solution (a solution with no analyte molecules 510 of interest). The high control portion preferably has a solution which has a known high concentration of analyte molecules 510 of interest.

The concentration of the analyte molecules 510 of interest within the sample solution 503 ("analyte concentration or [A]") may be determined as follows:

Determination of the Affinity Constant $K_A$

The affinity constant $K_A$ is a measure of how well antibodies couple to analytes. Under a preferred procedure, a value of $K_A$ is determined at the manufacturing level of cartridge 100 and applying the patches 180, 182, and 184. The value of $K_A$ and an error associated therewith is supplied to an end user (such as in a clinic or hospital) in, for example, a bar code that accompanies cartridge 100.

The value of a $K_A$ may be determined at the manufacturing level as follows. The fraction of bound antibody active sites ($f_b$) in a solution in cartridge 100 may be expressed in equation (1), below:

$$f_b = K_A[A]/(1+K_A[A]) \quad (1),$$

where $K_A$ is the affinity constant, and [A] is the analyte concentration.

Solutions of, for example, progressively larger known analyte concentrations $[A]_1, [A]_2, \ldots [A]_N$ are passed through an antibody well 116, 136, and 152 (one solution per well) of a particular cartridge 100 (in combination with an associated waveguide), referred to as cartridge 100-1. Photodetection means determine corresponding fluorescence intensities $I_{VAR1}, I_{VAR2}, \ldots, I_{VARN}$ associated with each of the varying concentration solutions. (Either only one photodetector per well or more than one photodetector per well can make measurements of intensity I.)

The process is repeated with progressively larger known analyte concentrations $[A]_1, [A]_2, \ldots, [A]_N$ passed through antibody wells 116, 136, and 152 of a cartridge 100-2, the photodetection means determines corresponding fluorescence intensities $I_{VAR1}, I_{VAR2}, \ldots, I_{VARN}$. Since a single test in each antibody well cartridges 100 are usually self-destructive to the antibody wells 116, 136, and 152 (or at least not cost effective to warrant stripping the bound analyte molecules from the capture molecules), it is preferable to use a plurality of cartridges 100 to generate the relationship (i.e. curve) between fraction of bound antibody active sites $f_b$ and concentration [A]. Using a plurality of cartridges 100 is also preferably from a quality control standpoint. Random selection of cartridges from a production run (wherein the same material lots are used to produce the cartridges) will render a statistically more accurate $f_b$ to [A] relationship (i.e., curve). Preferably, values for $I_{MIN}$ (zero or near zero concentration of the analyte of interest) and $I_{MAX}$ (maximum or saturated concentration of analyte of interest) are included in the known concentration solutions.

Thus, the values of $f_{b1}, f_{b2}, \ldots, f_{bN}$ are calculated according to equation (1) for each analyte concentration $[A]_1, [A]_2, \ldots, [A]_N$ for each of cartridges 100-1 through 100-X. The values of $f_{b1}$ for the various cartridges 100-1 through 100-X are average to create a $f_{b1-ave}$. Likewise, the values of $f_{b2}$ for the various cartridges 100-1 through 100-X are averaged to create a $f_{b2-ave}$, and so forth through the values of $f_{bN}$ being averaged to create a $f_{bN-ave}$.

The number "X" in cartridge 100-X may be a preset value based on experience and quality control considerations. Alternatively, the value of "X" may be increased if the standard deviation of various $f_b$ values is greater than a threshold. In that case, values of $f_b$ for additional cartridges would be determined and considered in a revised average.

In this respect, a relatively small number of cartridges from a batch of cartridges (or a group of batches of trays) are used to develop values $f_{b1-ave}$, $f_{b2-ave}$, and $f_{bN-ave}$ for the whole batch. The number of cartridges used in the determination of $f_{b1-ave}$, $f_{b2-ave}$, and $f_{bN-ave}$ vis-a-vis the total number of cartridges in a batch (or group of batches) will depend on various factors including the error that will be tolerated. That error will vary depending on the analyte of interest and other considerations. Well developed issues of quality control may also be considered.

Next, a value of $K_A$ should be determined from $f_{b1-ave}$, $f_{b2-ave}$, and $f_{bN-ave}$. Under equation (1), if $f_b=0.5$, then $K_A=1/[A]$. As an example, the affinity constant can be determined from matching $f_b$ and [A] through a non-linear curve fitting technique (such as the "least squares" method) on equation (1). $K_A$ may be used as a fitting parameter. $K_A$ is varied in the non-linear least squares process to determine a best fit. A standard error is also determined.

Alternatively, a best fit may be determined by applying the non-linear least squares technique for $I_{MIN}$, $I_{MAX}$, and $K_A$.

The value of $K_A$ and error may be encoded onto bar code that is supplied with each tray.

Determination of the [A] in the field

The assay device 1300 of FIG. 13 having a signal processing system may determine the analyte concentration as hereinafter described.

The invention also includes methods of manufacturing and using the device. The depicted assay device housing 1300 preferably includes a bar code reader or like device 1308. The reader 1308 is used to input factory calibration or like information into the assay device 1300 for each cartridge 1302. Thus, it is preferable to have the factory calibration attached or on each cartridge 1302. The calibration information is used to calculate the concentration of the analyte of interest using the fluoroluminescent intensity of the low control sample, the high control sample, and one of the test samples.

Referring to FIGS. 1 and 2, a solution having a minimum or zero analyte concentration is passed through the low control antibody well 136, a solution having a maximum analyte concentration is passed through the high control antibody well 152, and a solution having the analyte of interest is passed through the sample antibody well 116. The analyte concentration of the analyte of interest is unknown. The purpose of this aspect of the invention is to determine the analyte concentration of this analyte of interest.

Figure 13:
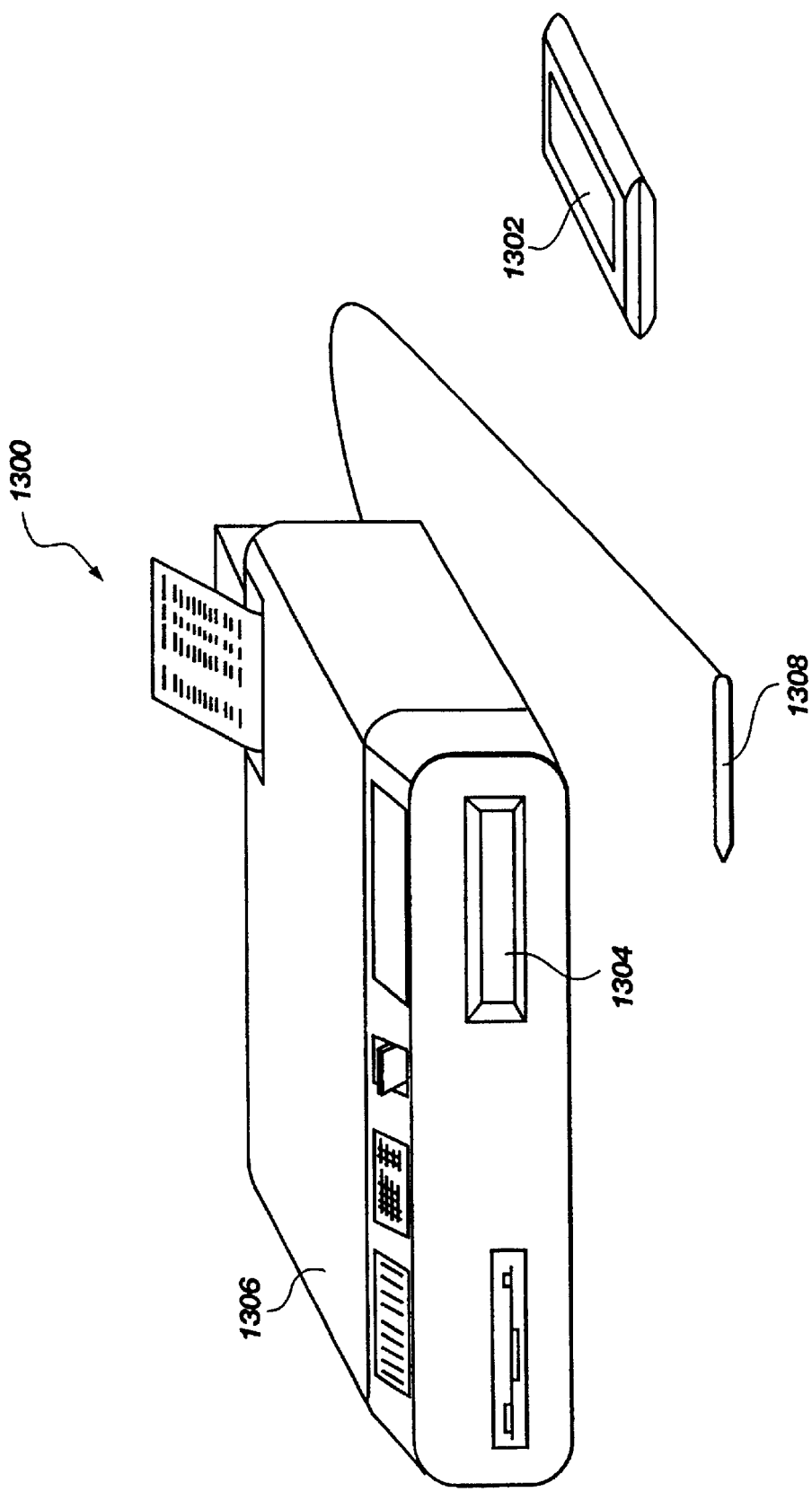
FIG. 13 is a top plan view of an assay device housing useful in the practice of the invention.

The photodetection means within the assay device 1300 of FIG. 13 measures the intensity of the fluorescent light to produce $I_{MIN}$ and $I_{MAX}$ for the particular solutions in wells 136 and 152, respectively. The photodetection means also measures the intensity of the fluorescent light to produce $I_{VAR}$ for the sample solution in the antibody well 116.

The value of $f_b$ is determined according to equation (2), below:

$$f_b=(I_{VAR}-I_{MIN})/(I_{MAX}-I_{MIN}) \qquad (2),$$

where $I_{VAR}$ is an intensity of fluorescent light radiated in response to evanescent light interacting with a solution having an unknown analyte concentration that is between a minimum and a maximum analyte concentration, inclusive; $I_{MIN}$ is the intensity of fluorescent light radiated in response to evanescent light encountering a solution having a minimum analyte concentration; $I_{MAX}$ is the intensity of fluorescent light radiated in response to evanescent light encountering a solution having a maximum analyte concentration.

The value of [A] may be solved for in equation (1), yielding equation (3), below:

$$[A]=f_b/((1-f_b)K_A) \qquad (3).$$

The value of $f_b$ is calculated, generally by a computer within the assay device 1300 in FIG. 13, according to equation (1) based on the measured values of $I_{MIN}$, $I_{VAR}$, and $I_{MAX}$ from wells 136, 152, and 116. The value of $f_b$ may be determined during the fabrication of the cartridges according to equation (1). The value of $K_A$ is read off a bar code by the reader 1308 of FIG. 13, or by some other means, and may be stored in memory of a computer associated with the assay device 1300. The analyte concentration of the solution of interest then may be calculated from equation (3).

A special case of equation (3) occurs where $[A]<<1/K_A$, in which case [A] is approximately $f_b/K_A$. Accordingly, an alternate computation may be used.

Two two-well biosensors (i.e., cartridges) may also be used to determine concentration. One biosensor would include $I_{MIN}$ and $I_{VAR-KNOWN}$ and the other biosensor would include $I_{MIN}$ and $I_{VAR-UNKNOWN}$. $I_{MAX}$ may be obtained from $I_{VAR-KNOWN}$ through equations (1) and (2). The two two-well biosensors may have greater value in large clinical labs that make many samples.

Data Fitting Function

A rate-based method may also be used. In such a method, the following formula may be used:

$$I_{(t)} = R_{ti}\frac{(e^{K*ti})(1-e^{-Kr})+I_o}{K}$$

wherein $(I_{(t)}, t)$ are intensity versus time data, $R_{ti}$ is the reaction rate at time ti, $I_o$ is intensity at time (t) equals 0, and K is the mass transport constant for a given waveguide, flow cell or reagent set (e.g. in the assay of FIG. 12, K is approximately 0.06 $M^{-1}$).

It is of course understood that these calculation techniques can be adapted and applied to any cartridge, tray, or the like when using the described analysis technique, such as the cartridges described in the present application, the trays described in Int'l Publ. No. 94/27137, or the like.

Having thus described in detail preferred embodiments of the present invention, it is to be understood that the invention is not to be limited by particular details set forth in the description as many apparent variations thereof are possible without departing from the spirit or scope thereof.

What is claimed is:

1. An assay cartridge for conducting homogeneous immunofluorescence assays comprising:
    a housing comprising:
        a sample apparatus having a port for receiving a fluid sample containing an unknown concentration of at least one analyte of interest, said port in fluid communication with a sample reagent well containing a predetermined sample reagent that interacts with said fluid sample and capture molecules, said sample reagent well in fluid communication with a sample capture molecule well, and a sample oscillation well for receiving, holding and releasing fluid during oscillation, said sample oscillation well in fluid communication with said sample capture molecule well; and
        a low control apparatus having a low control reagent well containing a predetermined low control reagent having a known low concentration, relative to the fluid sample, of at least one analyte of interest, said predetermined low control reagent interacting with capture molecules, said low control reagent well in fluid communication with a low control capture molecule well, and a low control oscillation well for receiving, holding and releasing fluid during oscillation, said low control oscillation well in fluid communication with said low control capture molecule well;
    said sample capture molecule well and said low control capture molecule well each having an adjacent wall including waveguide material; and
    at least one area containing capture molecules within each of said sample capture molecule well and said low control capture molecule well, wherein each of said capture molecule areas is attached to respective waveguide material.

2. The assay cartridge of claim 1 further comprising:
    a high control apparatus having a high control reagent well containing a predetermined high control reagent, which interacts with capture molecules, having a known high concentration, relative to said fluid sample, of at least one analyte of interest, said high control reagent well in fluid communication with a high control capture molecule well, and a high control oscillation well for receiving, holding and releasing fluid during oscillation, said high control oscillation well in fluid communication with said high control capture molecule well, said high control capture molecule well having a wall comprising waveguide material, and having at least one area containing capture molecules within said high control capture molecule well, wherein each of said capture molecule areas is attached to respective waveguide material.

3. An assay cartridge for conducting homogeneous immunofluorescence assays comprising:
    a housing comprising:
        a sample apparatus having a port for receiving a fluid sample containing an unknown concentration of at least one analyte of interest, said port in fluid communication with a sample reagent well containing a predetermined sample reagent, which interacts with said fluid sample and capture molecules, said sample reagent well in fluid communication with a sample capture molecule well, and a turbulence inducing means positioned between said sample reagent well and said sample capture molecule well; and
        a low control apparatus having a low control reagent well containing a predetermined low control reagent, which predetermined low control reagent interacts with capture molecules, having a known low concentration, relative to said fluid sample, of at least one analyte of interest, said low control reagent well in fluid communication with a low control capture molecule well, and a turbulence inducing means positioned between said low control reagent well and said low control capture molecule well;
    said sample capture molecule well and said low control capture molecule well each having an adjacent wall including waveguide material; and
    at least one area containing capture molecules within each of said sample capture molecule well and said low control capture molecule well, wherein each of said capture molecule areas is attached to respective waveguide material.

4. The assay cartridge of claim 3 further comprising:
    a high control apparatus having a high control reagent well containing a predetermined high control reagent, which predetermined high control reagent interacts with capture molecules, having a known high concentration, relative to said fluid sample, of at least one analyte of interest, said high control reagent well in fluid communication with a high control capture molecule well, and a turbulence inducing means positioned between said high control reagent well and said high control capture molecule well, said high control capture molecule well having a wall comprising waveguide material, and having at least one area containing capture molecules within said high control capture molecule well, wherein each of said capture molecule areas is attached to respective waveguide material.

5. The assay cartridge of claim 1 or claim 3, wherein said port is a sample cup.

6. The assay cartridge of claim 2 or claim 4, further comprising:
    a sample transfer means for transferring said fluid sample to said sample reagent well, and for transferring said fluid sample and said sample reagent from said sample reagent well to said sample capture molecule well;
    a low control transfer means for transferring said low control reagent to said low control capture molecule well; and
    a high control transfer means for transferring said high control reagent to said high control capture molecule well.

7. The assay cartridge of claim 6, further comprising:
    a first valve set between said sample cup and said sample reagent well, and between said sample reagent well and said sample capture molecule well;
    a second valve between said low control reagent well and said low control capture molecule well; and
    a third valve between said high control reagent well and said high control capture molecule well.

8. The assay cartridge of claim 2, further comprising:
a sample oscillation means for oscillating said fluid sample and said sample reagent between said sample reagent well and said sample oscillation well through said sample capture molecule well;
a low control oscillation means for oscillating said low control reagent between said low control reagent well and said low control oscillation well through said low control capture molecule well; and
a high control oscillation means for oscillating said high control reagent between said high control reagent well and said high control oscillation well through said high control capture molecule well.

9. The assay cartridge of claim 2 or claim 4, wherein the waveguide material of each of said sample capture molecule well, said low control capture molecule well, and said high control capture molecule well comprises a single waveguide, and said capture molecule wells include an opaque and rough wall surface opposing said waveguide.

10. The assay cartridge of claim 1 or claim 3, wherein said waveguide material comprises a single waveguide, said waveguide further comprising light receiving means on an edge thereof, said light receiving means configured to receive a light beam from a light source.

11. The assay cartridge of claim 10, wherein said waveguide further comprises light output means configured to output a portion of said beam received by said light receiving means.

12. The assay cartridge of claim 1 or claim 3, wherein said waveguide materials comprise a single waveguide detachably attached to said housing.

13. The assay cartridge of claim 1 or claim 3, wherein said capture molecules are selected from the group consisting of antibodies, antibody fragments, whole antigenic molecules, antigenic molecule fragments, oligopeptides, nucleic acids, oliogonucleotides, membrane receptors, peptides, and mixtures thereof.

14. The assay cartridge of claim 2 or claim 4, wherein said sample apparatus further includes a second sample reagent well containing a predetermined second reagent, said second sample reagent interacting with said fluid sample, said capture molecules and said sample reagent, in fluid communication with said sample reagent well and a sample waste well in fluid communication with said second sample reagent well and in fluid communication with said sample cup;
wherein said low control apparatus further includes a second low control reagent well containing a predetermined second low control reagent, that interacts with said capture molecules and said low control reagent, said second low control reagent well in fluid communication with said low control reagent well; and
wherein said high control apparatus further includes a second high control reagent well containing a predetermined second high control reagent, that interacts with said capture molecules and said high control reagent, said second high control reagent well in fluid communication with said high control reagent well.

15. The assay cartridge of claim 2, further comprising turbulence inducing means positioned in at least one of the following locations, between said sample reagent well and said sample capture molecule well, between said low control reagent well and said low control capture molecule well, and between said high control reagent well and said high control capture molecule well.

16. The assay cartridge of claim 4, further comprising:
a sample oscillation well for receiving, holding and releasing fluid during oscillation, in fluid communication with said sample capture molecule well;
a low control oscillation well for receiving, holding and releasing fluid during oscillation, said low control oscillation well in fluid communication with said low control capture molecule well; and
a high control oscillation well for receiving, holding and releasing fluid during oscillation, said high control oscillation well in fluid communication with said high control capture molecule well.

17. The assay cartridge of claim 2 or claim 16, further comprising turbulence inducing means positioned in at least one of the following locations, between said sample capture molecule well and said sample oscillation well, between said low control capture molecule well and said low control oscillation well, and between said high control capture molecule well and said high control oscillation well.

18. A method for conducting homogeneous immunofluorescence assays comprising:
providing an assay cartridge comprising:
a housing comprising:
a sample apparatus having a port for receiving a fluid sample containing an unknown concentration of at least one analyte of interest; said port in fluid communication with a first sample reagent well containing a predetermined sample reagent comprising tracer molecules having a fluorescent label thereon, said first sample reagent well in fluid communication with a sample capture molecule well, and a sample oscillation well for receiving, holding and releasing fluid during oscillation, said sample oscillation well in fluid communication with said sample capture molecule well; and
a low control apparatus having a first low control reagent well containing a predetermined low control reagent having a known low concentration, relative to said fluid sample, of at least one analyte of interest and tracer molecules having a fluorescent label thereon, said first low control reagent well in fluid communication with a low control capture molecule well, and a low control oscillation well for receiving, holding and releasing fluid during oscillation, said low control oscillation well in fluid communication with said low control capture molecule well;
waveguide means forming an adjacent wall of each of said sample capture molecule well and said low control capture molecule well wherein said waveguide means includes a receiving lens on an edge thereof, configured to receive a beam from a light source; and
at least one area containing capture molecules within each of said sample capture molecule well and said low control capture molecule well, wherein said capture molecule areas are attached to said waveguide means;
introducing a predetermined quantity of a sample fluid in said port;
transferring said sample fluid into said first sample reagent well to mix with said predetermined sample reagent;
transferring said sample fluid/sample reagent mixture into said sample capture molecule well to contact the sample fluid/sample reagent mixture with said sample capture molecule well capture molecule areas;

transferring said low control reagent mixture into said low control capture molecule well to contact said low control reagent mixture with said low control capture molecule well capture molecule areas;

transmitting a light beam into said receiving lens of said waveguide means, wherein said light beam travels a length of said waveguide means, and interacts with tracer molecules which have interacted with said capture molecules causing them to fluoresce; and determining the concentration of said at least one analyte of interest in said sample fluid by a comparison of intensities of fluorescence between said capture molecule areas of said sample capture molecule well and said low control capture molecule well.

19. The method of claim 18 wherein the housing further comprises:

a high control apparatus having a first high control reagent well containing a predetermined high control reagent having a known high concentration, relative to said fluid sample, of at least one analyte of interest, and tracer molecules having a fluorescent label thereon, said first high control reagent well in fluid communication with a high control capture molecule well, and a high control oscillation well for receiving, holding and releasing fluid during oscillation, said high control oscillation well in fluid communication with said high control capture molecule well, said first high control capture molecule well having a wall comprising waveguide material, and having at least one area containing capture molecules within said first high control capture molecule well;

and the method further comprises:

transferring said high control reagent mixture into said high control capture molecule well to contact said high control reagent mixture with said high control capture molecule well capture molecule areas.

20. A method for conducting homogeneous immunofluorescence assays comprising:

providing an assay cartridge comprising:

a housing comprising:

a sample apparatus having a port for receiving a fluid sample containing an unknown concentration of at least one analyte of interest; said port in fluid communication with a sample waste well, said sample waste well in fluid communication with a second sample reagent well containing a predetermined second sample reagent, which second sample reagent interacts with said fluid sample, a first sample reagent and capture molecules, said second sample reagent in fluid communication with a first sample reagent well containing a predetermined first sample reagent comprising tracer molecules, said first sample reagent well in fluid communication with a sample capture molecule well, and a sample oscillation well for receiving, holding and releasing fluid during oscillating, said sample oscillation well in fluid communication with said sample capture molecule well; and a low control apparatus having a second low control reagent well containing a predetermined second low control reagent having a known low concentration, relative to said fluid sample, of at least one analyte of interest, said second low control reagent interacting with capture molecules and a first low control reagent, said second low control reagent well in fluid communication with a first low control reagent well containing a predetermined first low control reagent comprising tracer molecules, said first low control reagent well in fluid communication with a low control capture molecule well, and a low control oscillation well in fluid communication with said low control capture molecule well, said low control oscillation well for receiving, holding and releasing fluid during oscillation;

a waveguide forming an adjacent wall of each of said sample capture molecule well and said low control capture molecule well wherein said waveguide includes a receiving lens on an edge of said waveguide configured to receive a beam from a light source; and at least one area containing capture molecules within each of said sample capture molecule well and said low control capture molecule well, wherein each of said capture molecule areas is attached to said waveguide;

depositing a predetermined quantity of a sample fluid in said assay cartridge port;

transferring said sample fluid into said second sample reagent well to mix with said second sample reagent;

transferring said sample fluid/second sample reagent mixture into said first sample reagent well to mix with said first sample reagent;

transferring said sample fluid/second sample reagent/first sample reagent mixture into said sample capture molecule well to contact the sample fluid/second sample reagent/first sample reagent mixture with said sample capture molecule well capture molecule areas;

transferring said second low control reagent into said first low control reagent well to contact said second low control reagent with said first low control reagent;

transferring said second low control reagent/first low control reagent mixture into said low control capture molecule well to contact said second low control reagent/first low control reagent mixture with said low control capture molecule well capture molecule areas;

transmitting a light beam into said receiving lens of said waveguide means, wherein said light beam travels a length of said waveguide, and interacts with tracer molecules which have been captured by said capture molecules, causing them to fluoresce; and determining the concentration of said analyte of interest in said sample fluid by comparing intensities of fluorescence between said capture molecule areas of said sample capture molecule well and said low control capture molecule well.

21. The method of claim 20 wherein the housing of the assay cartridge further comprises:

a high control apparatus having a second high control reagent well containing a predetermined second high control reagent having a known high concentration, relative to said sample fluid, of at least one analyte of interest, said second high control reagent interacting with a first high control reagent and capture molecules, said second high control reagent well in fluid communication with a first high control reagent well containing a predetermined first high control reagent comprising tracer molecules, said first high control reagent well in fluid communication with a high control capture molecule well, and a high control oscillation well in fluid communication with said high control capture molecule well, said high control oscillation well for receiving, holding and releasing fluids during oscillation, said first high control capture molecule well having a wall comprising waveguide material, and having at least one area containing capture molecules within said first high control capture molecule well;

and the method further comprises:

transferring said second high control reagent into said first high control reagent well to contact said second high control reagent with said first high control reagent; and transferring said second high control reagent/first high control reagent mixture into said high control capture molecule well to contact said second high control reagent first high control reagent mixture with said high control capture molecule well capture molecule areas; and the concentration of the analyte of interest in said sample fluid is compared with the intensity of fluorescence in the high control capture molecule well.

22. A method for conducting homogeneous immunofluorescence assays comprising:

providing an assay cartridge comprising:

a housing comprising:

a sample apparatus having a port for receiving a fluid sample containing an unknown concentration of at least one analyte of interest; said port in fluid communication with a first sample reagent well containing a predetermined sample reagent comprising tracer molecules having a fluorescent label thereon, said first sample reagent well in fluid communication with a sample capture molecule well, and a turbulence inducing means positioned between said first sample reagent well and said sample capture molecule well; and a low control apparatus having a first low control reagent well containing a predetermined low control reagent having a known low concentration, relative to the fluid sample, of at least one analyte of interest, said low control reagent comprising tracer molecules having a fluorescent label thereon, said first low control reagent well in fluid communication with a low control capture molecule well, and a turbulence inducing means positioned between said first low control reagent well and said low control capture molecule well;

waveguide means forming an adjacent wall of each of said sample capture molecule well and said low control capture molecule well wherein said waveguide means includes a receiving lens on an edge thereof, configured to receive a beam from a light source; and at least one area containing capture molecules within each of said sample capture molecule well and said low control capture molecule well, wherein said capture molecule areas are attached to said waveguide means;

introducing a predetermined quantity of a sample fluid in said port;

transferring said sample fluid into said first sample reagent well to mix with said sample reagent;

transferring said sample fluid/sample reagent mixture into said sample capture molecule well to contact the sample fluid/sample reagent mixture with said sample capture molecule well capture molecule areas;

transferring said low control reagent mixture into said low control capture molecule well to contact said low control reagent mixture with said low control capture molecule well capture molecule areas;

transmitting a light beam into said receiving lens of said waveguide means, wherein said light beam travels a length of said waveguide, and interacts with tracer molecules which have interacted with said capture molecules causing them to fluoresce; and determining the concentration of said analyte of interest in said sample fluid by a comparison of intensities of fluorescence between said capture molecule areas of said sample capture molecule well and said low control capture molecule well.

23. The method of claim 22 wherein the housing further comprises:

a high control apparatus having a first high control reagent well containing a predetermined high control reagent having a known high concentration, relative to said fluid sample, of at least one analyte of interest, said high control reagent comprising tracer molecules having a fluorescent label thereon, said first high control reagent well in fluid communication with a high control capture molecule well, and a turbulence inducing means positioned between said first high control reagent well and said high control capture molecule well, said first high control capture molecule well having a wall comprising waveguide material, and having at least one area having capture molecules within said first high control capture molecule well;

and the method further comprises:

transferring said high control reagent mixture into said high control capture molecule well to contact said high control reagent mixture with said high control capture molecule well capture molecule areas.

24. A method for conducting homogeneous immunofluorescence assays comprising:

providing an assay cartridge comprising:

a housing comprising:

a sample apparatus having a port for receiving a fluid sample containing an unknown concentration of at least one analyte of interest; said port in fluid communication with a sample waste well, said sample waste well in fluid communication with a second sample reagent well containing a predetermined second sample reagent, which second sample reagent reacts with said fluid sample, a first sample reagent and capture molecules, said second sample reagent in fluid communication with a first sample reagent well containing a predetermined first sample reagent comprising tracer molecules, said first sample reagent well in fluid communication with a sample capture molecule well, and a turbulence inducing means positioned between said first sample reagent well and said sample capture molecule well; and a low control apparatus having a second low control reagent well containing a predetermined second low control reagent having a known low concentration, relative to said fluid sample, of at least one analyte of interest, said second low control reagent reacts with a first low control reagent and capture molecules, said second low control reagent well in fluid communication with a first low control reagent well containing a predetermined first low control reagent comprising tracer molecules, said first low control reagent well in fluid communication with a low control capture molecule well, and a turbulence inducing means positioned between said first low control reagent well and said low control capture molecule well;

a waveguide forming an adjacent wall of each of said sample capture molecule well and said low control capture molecule well wherein said waveguide includes a receiving lens on an edge of said waveguide configured to receive a beam from a light source; and at least one area containing capture molecules within each of said sample capture molecule well and said low control capture molecule well, wherein each of said capture molecule areas is attached to said waveguide;

depositing a predetermined quantity of a sample fluid in said port;

transferring said sample fluid into said second sample reagent well to mix with said second sample reagent;

transferring said sample fluid/second sample reagent mixture into said first sample reagent well to mix with said first sample reagent;

transferring said sample fluid/second sample reagent/first sample reagent mixture into said sample capture molecule well to contact the sample fluid/second sample reagent/first sample reagent mixture with said sample capture molecule well capture molecule areas;

transferring said second low control reagent into said first low control reagent well to contact said second low control reagent with said first low control reagent;

transferring said second low control reagent/first low control reagent mixture into said low control capture molecule well to contact said second low control reagent/first low control reagent mixture with said low control capture molecule well capture molecule areas;

transmitting a light beam into said receiving lens of said waveguide, wherein said light beam travels a length of said waveguide, and interacts with tracer molecules which have been captured by said capture molecules, causing them to fluoresce; and determining the concentration of said analyte of interest in said sample fluid by comparing intensities of fluorescence between said capture molecule areas of said sample capture molecule well and said low control capture molecule well.

25. The method of claim 24 wherein the housing of the assay cartridge further comprises:

a high control apparatus having a second high control reagent well containing a predetermined second high control reagent having a known high concentration, relative to the fluid sample, of at least one analyte of interest, said second high control reagent interacting with a first high control reagent and capture molecules, said second high control reagent well in fluid communication with a first high control reagent well containing a predetermined first high control reagent comprising tracer molecules, said first high control reagent well in fluid communication with a high control capture molecule well, and a turbulence inducing means positioned between said first high control reagent well and said high control capture molecule well, said first high control capture molecule well having a wall comprising waveguide material, and having at least one area containing capture molecules within said first high control capture molecule well;

and the method further comprises:

transferring said second high control reagent into said first high control reagent well to contact said second high control reagent with said first high control reagent; and transferring said second high control reagent/first high control reagent mixture into said high control capture molecule well to contact said second high control reagent/first high control reagent mixture with said high control capture molecule well capture molecule areas; and the concentration of the analyte of interest in said sample fluid is compared with the intensity of fluorescence in the high control capture molecule well.

26. The method of claim 21 or claim 25, further comprising:

transferring said sample fluid/second sample reagent/first sample reagent mixture between the first sample reagent well and the second sample reagent well to mix the sample solution/first reagent/second reagent mixture;

transferring said second low control reagent/first low control reagent mixture between the first low control reagent well and the second low control reagent well to mix the second low control reagent/first low control reagent mixture; and transferring said second high control reagent/first high control reagent mixture between the first high control reagent well and the second high control reagent well to mix the second high control reagent/first high control reagent mixture.

27. The method of claim 23 or claim 25, wherein said assay cartridge used in said method further comprises:

a sample oscillation well for receiving, holding and releasing fluid during oscillation, said sample oscillation well in fluid communication with said sample capture molecule well;

a low control oscillation well for receiving, holding and releasing fluid during oscillation, said low control oscillation well in fluid communication with said low control capture molecule well; and a high control oscillation well for receiving, holding and releasing fluid during oscillation, said high control oscillation well in fluid communication with said high control capture molecule well.

28. The method of claim 19 or claim 21, further comprising:

oscillating said fluid sample/second sample reagent/first sample reagent mixture between said first sample reagent well and said sample oscillation well through said sample capture molecule well prior to fluorescence detection;

oscillating said second low control reagent/first low control reagent mixture between said first low control reagent well and said low control oscillation well through said low control capture molecule well prior to fluorescence detection; and oscillating said second high control reagent/first high control reagent mixture between said first high control reagent well and said high control oscillation well through said high control capture molecule well prior to fluorescence detection.

29. The method of claim 19, claim 21, claim 23, or claim 25, wherein each of said sample capture molecule well, said low control capture molecule well, and said high control capture molecule well include an opaque and rough wall surface opposing said waveguide.

30. The method of claim 18, claim 20, claim 22, or claim 24, wherein said waveguide further comprises an output lens configured to output a portion of said beam received from said receiving lens.

31. The method of claim 18, claim 20, claim 22, or claim 24, wherein said capture molecules are selected from the group consisting of antibodies, antibody fragments, whole antigenic molecules, antigenic molecule fragments, oligopeptides, nucleic acids, oliogonucleotides, membrane receptors, peptides, and mixtures thereof.

32. The method of claim 19 or claim 21, wherein said assay cartridge further comprises turbulence inducing means positioned in at least one of the following locations, between said first sample reagent well and said sample capture molecule well, between said first low control reagent well and said low control capture molecule well, and between said first high control reagent well and said high control capture molecule well.

33. The method of claim 19 or claim 21, wherein said assay cartridge further comprises turbulence inducing means positioned in at least one of the following locations, between said sample capture molecule well and said sample oscillation well, between said low control capture molecule well and said low control oscillation well, and between said high control capture molecule well and said high control oscillation well.

34. The method of claim 18 or claim 22, wherein the step of transferring said sample fluid into said first sample reagent well to mix with said sample reagent further includes shifting at least a portion of the sample fluid/sample reagent mixture between said first sample reagent well and said port to mix the sample fluid/sample reagent mixture.

35. A method for conducting homogeneous immunofluorescence assays comprising providing an assay cartridge including a housing comprising an opening for receiving a fluid sample and at least one area containing capture molecules attached to a waveguide material, and introducing said fluid sample containing an unknown concentration of at least one analyte of interest such that said fluid sample contacts said capture molecule, an improvement comprising: oscillating said fluid sample over said capture molecules.

36. A method for conducting homogeneous immunofluorescence assays comprising providing an assay cartridge including a housing comprising an opening for receiving a fluid sample and at least one area containing capture molecules attached to a waveguide material, and introducing a fluid sample containing an unknown concentration of at least one analyte of interest such that said fluid sample contacts said capture molecule, an improvement comprising: inducing turbulent flow of said fluid sample over said capture molecules.

37. The assay cartridge of claim 16, further comprising:
a sample oscillation means for oscillating said fluid sample and said sample reagent between said sample reagent well and said sample oscillation well through said sample capture molecule well;
a low control oscillation means for oscillating said low control reagent between said low control reagent well and said low control oscillation well through said low control capture molecule well; and
a high control oscillation means for oscillating said high control reagent between said high control reagent well and said high control oscillation well through said high control capture molecule well.

* * * * *